(12) United States Patent
Béalle et al.

(10) Patent No.: US 10,808,170 B2
(45) Date of Patent: Oct. 20, 2020

(54) ESTERS CONTAINING NON-AROMATIC CYCLES AS SOLVENTS FOR OLED FORMULATIONS

(71) Applicant: Merck Patent GmbH, Darmstadt (DE)

(72) Inventors: Gaëlle Béalle, Heidelberg (DE); Christoph Leonhard, Otzberg (DE); Hsin-Rong Tseng, Frankfurt am Main (DE); Irina Martynova, Greisheim (DE); Aurélie Ludemann, Frankfurt am Main (DE)

(73) Assignee: Merck Patent GmbH (DE)

( * ) Notice: Subject to any disclaimer, the term of this patent is extended or adjusted under 35 U.S.C. 154(b) by 360 days.

(21) Appl. No.: 15/735,013

(22) PCT Filed: May 13, 2016

(86) PCT No.: PCT/EP2016/000797
§ 371 (c)(1),
(2) Date: Dec. 8, 2017

(87) PCT Pub. No.: WO2016/198141
PCT Pub. Date: Dec. 15, 2016

(65) Prior Publication Data
US 2018/0155616 A1    Jun. 7, 2018

(30) Foreign Application Priority Data
Jun. 12, 2015    (EP) .................................... 15001741

(51) Int. Cl.
| | |
|---|---|
| C09K 11/06 | (2006.01) |
| H01L 51/00 | (2006.01) |
| C07C 69/013 | (2006.01) |
| C07C 69/22 | (2006.01) |
| C09K 11/02 | (2006.01) |

(52) U.S. Cl.
CPC ............ C09K 11/06 (2013.01); C07C 69/013 (2013.01); C07C 69/22 (2013.01); C09K 11/025 (2013.01); H01L 51/0007 (2013.01); C09K 2211/1029 (2013.01); C09K 2211/185 (2013.01)

(58) Field of Classification Search
CPC ....... C09K 11/02; C09K 11/025; C09K 11/06; C07C 69/013; C07C 69/22; H01L 51/0007
See application file for complete search history.

(56) References Cited

U.S. PATENT DOCUMENTS

| | | | |
|---|---|---|---|
| 6,023,371 A * | 2/2000 | Onitsuka | C09K 11/025 250/458.1 |
| 2006/0145163 A1* | 7/2006 | Tsujimura | H01L 27/3211 257/79 |
| 2007/0075630 A1* | 4/2007 | Dotz | H01L 51/0541 313/504 |
| 2010/0323464 A1 | 12/2010 | Cheon et al. | |
| 2011/0176095 A1 | 7/2011 | Fujita et al. | |
| 2011/0220886 A1 | 9/2011 | Takeshima et al. | |
| 2014/0087507 A1 | 3/2014 | Tregub et al. | |
| 2014/0097406 A1 | 4/2014 | Cheon et al. | |
| 2015/0044802 A1 | 2/2015 | Tregub et al. | |
| 2015/0053892 A1 | 2/2015 | Takeda et al. | |
| 2015/0333269 A1 | 11/2015 | Suzuki et al. | |

FOREIGN PATENT DOCUMENTS

| | | |
|---|---|---|
| CN | 103782237 A | 5/2014 |
| JP | H1033872 A | 2/1998 |
| JP | 2008214452 A | 9/2008 |
| JP | 2013018770 A | 1/2013 |
| JP | 2018095661 A | 6/2018 |
| WO | WO-2016125618 A1 | 8/2016 |

OTHER PUBLICATIONS

Burgués-Ceballos, I., et al., "Solubility Based Identification of Green Sovlents for Small Molecule Organic Solar Cells", Advanced Functional Materials, vol. 24, No. 10, (2014), pp. 1449-1457.
International Search Report for PCT/EP2016/000797 dated Aug. 19, 2016.
Magens, S., et al., "Nucleophilic Iron Catalysis in Transesterifications: Scope and Limitations", Journal of Organic Chemistry, vol. 75, No. 11, (2010), pp. 3715-3721.
Schwenninger, R., et al., "Metal Complexes of a Biconcave Porphyrin with D4-Structure-Versatile Chiral Shift Agents", Chemistry: a European Journal, vol. 7, No. 12, (2001), pp. 2676-2686.
Written Opinion of the International Searching Authority for PCT/EP2016/000797 dated Aug. 19, 2016.

* cited by examiner

*Primary Examiner* — C Melissa Koslow
(74) *Attorney, Agent, or Firm* — Faegre Drinker Biddle & Reath LLP

(57) ABSTRACT

The present invention relates to formulations for the preparation of organic electronic devices (OLEDs) which comprise at least one specific ester solvent containing a non aromatic cycle and at least one organic functional material selected from organic conductors, organic semiconductors, organic fluorescent compounds, organic phosphorescent compounds, organic light-absorbent compounds, organic light-sensitive compounds, organic photosensitisation agents and other organic photoactive compounds, selected from organometallic complexes of transition metals, rare earths, lanthanides and actinides.

21 Claims, 1 Drawing Sheet

Figure 1:

| | |
|---|---|
| 100 nm | Al Cathode |
| 20 nm | ETL |
| 20 nm | B-CML |
| 60 nm | G-EML (Reference, Example 1,2,3,4) |
| 20 nm | HTL |
| 30 nm | HIL |
| 50 nm | ITO Anode |
| | Substrate |

Figure 2:

| | |
|---|---|
| 100 nm | Al Cathode |
| 40 nm | ETL |
| 10 nm | HBL |
| 60 nm | G-EML |
| 20 nm | HTL |
| 30 nm | HIL |
| 50 nm | ITO Anode |
| | Substrate |

ESTERS CONTAINING NON-AROMATIC CYCLES AS SOLVENTS FOR OLED FORMULATIONS

CROSS-REFERENCE TO RELATED APPLICATIONS

This application is a national stage application (under 35 U.S.C. § 371) of PCT/EP2016/000797, filed May 13, 2016, which claims benefit of European Application No. 15001741.6, filed Jun. 12, 2015, both of which are incorporated herein by reference in their entirety.

TECHNICAL FIELD

The present invention relates to formulations for the preparation of organic electronic devices (OLEDs) which comprise at least one ester solvent containing a non aromatic cycle and at least one specific organic functional material. The formulation is particularly suitable for the preparation of OLEDs by inkjet printing or spin coating processes.

BACKGROUND ART

Organic Light Emitting Devices (OLEDs) have been fabricated for a long time by vacuum deposition processes. Other techniques such as inkjet printing have been recently thoroughly investigated because of their advantages such as cost savings and scale-up possibilities. One of the main challenges in multi-layer printing is to identify and adjust the relevant parameters to obtain a homogeneous deposition of inks on the substrate coupled with good device performances. In particular, solubility of materials, physical parameters of the solvent (surface tension, viscosity, boiling point, etc.), printing technology, processing conditions (air, nitrogen, temperature, etc.) and drying parameters are characteristics which can drastically influence the pixel pattern and thus the device performances. Among these features, solvent choice is crucial. As an example, US 2015/0044802 describes ink compositions for forming active layers in an organic light-emitting diode. The compositions contain an ester-based solvent system comprising at least one ester selected from alkyl octanoates, alkyl sebacates or combinations thereof. In a similar way, US 2011/0220886 A1 describes organic electroluminescence material compositions which include a solvent having an aliphatic ring or an aromatic ring and an anthracene derivative. As an example, indene or indane were used as solvent in the organic electroluminescence materials compositions.

Technical Problem and Object of the Invention

Many solvents have been proposed in organic electronic devices for inkjet printing. However, the number of important parameters playing a role during deposition and the drying process makes the choice of the solvent very challenging. Thus, the formulations containing organic functional materials such as semiconductors used for deposition by inkjet printing still need to be improved. One object of the present invention is to provide a formulation of an organic functional material which allows a controlled deposition to form organic semiconductor layers having good layer properties and performance. A further object of the present invention is to provide a formulation of an organic functional material which allows an uniform application of ink droplets on a substrate when used in an inkjet printing method thereby giving good layer properties and performance.

Solution to Problem

The above-mentioned objects of the present invention are solved by providing a formulation comprising at least one ester solvent according to General Formula (I) or General Formula (II):

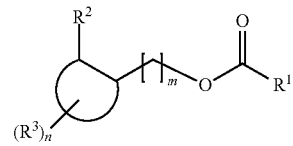

General Formula (I)

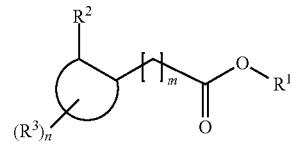

General Formula (II)

wherein

is a non-aromatic cyclic alkyl or alkenyl group having from 3 to 20 carbon atoms, preferably from 4 to 12 carbon atoms and more preferably from 5 to 8 carbon atoms, to which the substituents $R^2$, $R^3$ and $-[CH_2]_m-O-CO-R^1$ or $-[CH_2]_m-CO-O-R^1$ are bound as shown in General Formulae (I) and (II), respectively, in which one or more hydrogen atoms may be optionally replaced by F and in which one or more non-adjacent $CH_2$ groups may be optionally replaced by $-O-$;

$R^1$ and $R^2$ may be the same or different from each other and are independently selected from the group consisting of hydrogen, straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atom may be optionally replaced by F and wherein one or more non-adjacent $CH_2$ groups may be optionally replaced by $-O-$ or $-Si(R^4)_2-$;

$R^3$ may be identical or different at each occurrence and is selected from the group consisting of straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by $-O-$ or $-Si(R^4)_2-$ and/or a plurality of $R^3$ may together form a mono- or polycyclic aliphatic ring system;

$R^4$ is identical or different at each occurrence and is selected from the group consisting of hydrogen, straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by —O—, —(C=O)—O— or —(C=O)—;

m is an integer from 0 to 5, preferably from 0 to 3; and n is an integer from 0 to 2x-2, wherein x is the number of carbon atoms in the non-aromatic cyclic alkyl or alkenyl group

;

and at least one organic functional material selected from the group consisting of organic conductors, organic semiconductors, organic fluorescent compounds, organic phosphorescent compounds, organic light-absorbent compounds, organic light-sensitive compounds, organic photosensitisation agents and other organic photoactive compounds, selected from organometallic complexes of transition metals, rare earths, lanthanides and actinides.

Advantageous Effects of Invention

The inventors have surprisingly found that the use of an ester containing a non-aromatic cycle as solvent for OLED formulations allows an effective ink deposition to form uniform and well-defined organic layers of functional materials which have good layer properties and very good performance.

BRIEF DESCRIPTION OF DRAWINGS

FIG. 1 shows a typical layer structure of a device containing a substrate, an ITO anode, a hole-injection layer (HIL), a hole-transport layer (HTL), a green-emissive layer (G-EML), a blue common layer (BCL), an electron-transport layer (ETL) and an Al cathode.

FIG. 2 shows the layer structure of a device which is used in Examples 5 to 11 and Reference 1. The device contains a substrate, an ITO anode, a hole-injection layer (HIL), a hole-transport layer (HTL), a green-emissive layer (G-EML), a hole-blocking layer (HBL), an electron-transport layer (ETL) and an Al cathode.

DESCRIPTION OF EMBODIMENTS

The present invention relates to a formulation comprising at least one ester solvent according to General Formula (I) or General Formula (II):

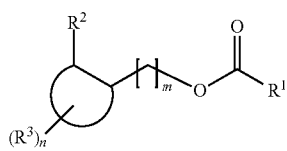

General Formula (I)

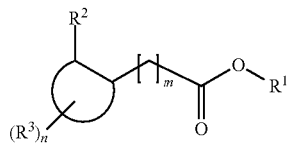

General Formula (II)

wherein

is a non-aromatic cyclic alkyl or alkenyl group having from 3 to 20 carbon atoms, preferably from 4 to 12 carbon atoms and more preferably from 5 to 8 carbon atoms, to which the substituents $R^2$, $R^3$ and —$[CH_2]_m$—O—CO—$R^1$ or —$[CH_2]_m$—CO—O—$R^1$ are bound as shown in General Formulae (I) and (II), respectively, in which one or more hydrogen atoms may be optionally replaced by F and in which one or more non-adjacent $CH_2$ groups may be optionally replaced by —O—;

$R^1$ and $R^2$ may be the same or different from each other and are independently selected from the group consisting of hydrogen, straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atom may be optionally replaced by F and wherein one or more non-adjacent $CH_2$ groups may be optionally replaced by —O— or —Si($R^4$)$_2$—;

$R^3$ may be identical or different at each occurrence and is selected from the group consisting of straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by —O— or —Si($R^4$)$_2$— and/or a plurality of $R^3$ may together form a mono- or polycyclic aliphatic ring system;

$R^4$ is identical or different at each occurrence and is selected from the group consisting of hydrogen, straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by —O—, —(C=O)—O— or —(C=O)—;

m is an integer from 0 to 5, preferably from 0 to 3; and n is an integer from 0 to 2x-2, wherein x is the number of carbon atoms in the non-aromatic cyclic alkyl or alkenyl group

;

and at least one organic functional material selected from the group consisting of organic conductors, organic semiconductors, organic fluorescent compounds, organic phosphorescent compounds, organic light-absorbent compounds, organic light-sensitive compounds, organic photosensitisation agents and other organic photoactive compounds, selected from organometallic complexes of transition metals, rare earths, lanthanides and actinides.

PREFERRED EMBODIMENTS

In a first preferred embodiment, the ester solvent is represented by General Formula (I).

In a second preferred embodiment, the ester solvent is represented by General Formula II.

Preferably, the structural element

in General Formulae (I) and (II) is a non-aromatic cyclic alkyl or alkenyl group having from 4 to 12 carbon atoms, more preferably from 5 to 8 carbon atoms, to which the substituents $R^2$, $R^3$ and $-[CH_2]_m-O-CO-R^1$ or $-[CH_2]_m-CO-O-R^1$ are bound as shown in General Formulae (I) and (II), respectively, in which one or more hydrogen atoms may be optionally replaced by F and in which one or more non-adjacent $CH_2$ groups may be optionally replaced by $-O-$.

Most preferably, the structural element

in General Formulae (I) and (II) is selected from

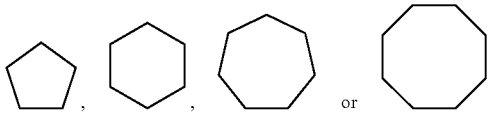

to which the substituents $R^2$, $R^3$ and $-[CH_2]_m-O-CO-R^1$ or $-[CH_2]_m-CO-O-R^1$ are bound as shown in General Formulae (I) and (II), respectively.

Preferably, $R^1$, $R^2$ and each of $R^3$ in General Formulae (I) and (II) are independently selected from the group consisting of hydrogen and alkyl groups having from 1 to 10 carbon atoms with the provision that $R^3$ is not hydrogen. Alkyl groups having from 1 to 10 carbon atoms include methyl, ethyl, propyl, butyl, pentyl, hexyl, heptyl, octyl, nonyl and decyl and their isomers.

More preferably, $R^1$, $R^2$ and each of $R^3$ in General Formulae (I) and (II) are independently selected from the group consisting of hydrogen, methyl, ethyl, 1-propyl, 2-propyl, n-butyl, iso-butyl, sec-butyl, t-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 3-methylpentyl, 4-methylpentyl, 2-methylpent-2-yl, 3-methylpent-2-yl, 2-methylpent-3-yl, 3-methylpent-3-yl, 2-ethylbutyl, 3-ethylbutyl, 2,3-dimethylbutyl, 2,3-dimethylbut-2-yl, 2,2-dimethylbutyl, n-heptyl, n-octyl, n-nonyl and n-decyl with the provision that $R^3$ is not hydrogen.

Preferably, $R^4$ is identical or different at each occurrence and is selected from the group consisting of hydrogen, straight-chain alkyl or alkenyl groups having from 1 to 10 carbon atoms, branched-chain alkyl or alkenyl groups having from 3 to 10 carbon atoms, cyclic alkyl or alkenyl groups having from 3 to 10 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by $-O-$, $-(C=O)-O-$ or $-(C=O)-$.

More preferably, $R^4$ is identical or different at each occurrence and is selected from the group consisting of hydrogen and alkyl groups having from 1 to 10 carbon atoms such as methyl, ethyl, propyl, butyl, pentyl, hexyl, heptyl, octyl, nonyl and decyl and their isomers.

Most preferably, $R^4$ is identical or different at each occurrence and is selected from the group consisting of hydrogen, methyl, ethyl, 1-propyl, 2-propyl, n-butyl, iso-butyl, sec-butyl, t-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 3-methylpentyl, 4-methylpentyl, 2-methylpent-2-yl, 3-methylpent-2-yl, 2-methylpent-3-yl, 3-methylpent-3-yl, 2-ethylbutyl, 3-ethylbutyl, 2,3-dimethylbutyl, 2,3-dimethylbut-2-yl, 2,2-dimethylbutyl, n-heptyl, n-octyl, n-nonyl and n-decyl.

Examples of the most preferred ester solvents, their boiling points (BP) and physical state at room temperature are shown in Table 1 below.

TABLE 1

Most preferred ester solvents, their boiling points (BP) and their physical state at room temperature (25° C.).

| Ester Solvent | BP (° C.) (760 mm Hg) | Physical State at RT |
|---|---|---|
| Cyclohexyl hexanoate | 255 | Liquid at RT |
| Cyclohexyl butyrate | 214 | Liquid at RT |
| Ethyl cyclohexylacetate | 211 | Liquid at RT |
| Cyclohexyl isovalerate | 223 | Liquid at RT |

TABLE 1-continued

Most preferred ester solvents, their boiling points (BP) and their physical state at room temperature (25° C.).

| Ester Solvent | BP (° C.) (760 mm Hg) | Physical State at RT |
|---|---|---|
| 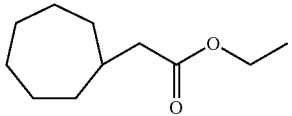<br>Ethyl cycloheptylacetate | 232 | Liquid at RT |
| 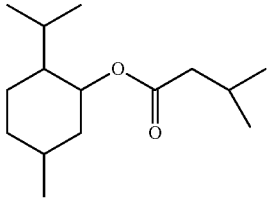<br>Menthyl isovalerate | 260 | Liquid at RT |
| 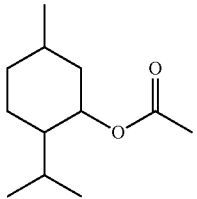<br>Menthyl acetate | 229 | Liquid at RT |
| 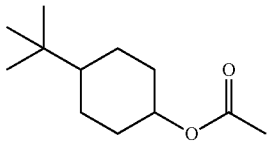<br>4-tert-butylcyclohexyl acetate | 222 | Liquid at RT |
| 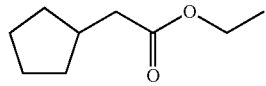<br>Ethyl cyclopentylacetate | 196 | Liquid at RT |
| 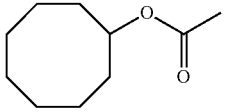<br>Cyclooctyl acetate | 215 | Liquid at RT |
| 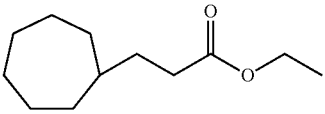<br>Ethyl cycloheptylacetate | 232 | Liquid at RT |

Preferably, the ester solvent according to General Formula (I) or (II) is liquid at room temperature which means that it has a melting point of 25° C. or below.

Preferably, the ester solvent according to General Formulae (I) and (II) has a boiling point of 400° C. or below, preferably in the range from 100° C. to 350° C., more preferably in the range from 150° C. to 350° C. and most preferably in the range from 200° C. to 300° C., wherein the boiling point is given at 760 mm Hg.

Preferably, the formulation has a surface tension in the range from 1 to 70 mN/m, preferably in the range from 10 to 50 mN/m and more preferably in the range from 20 to 40 mN/m.

The surface tension of the formulations of the present invention is measured by pendant drop characterization which is an optical method.

This measurement technique dispenses a drop from a needle in a bulk gaseous phase. The shape of the drop results from the relationship between the surface tension, gravity and density differences. Using the pendant drop method, the surface tension is calculated from the shadow image of a pendant drop using drop shape analysis. A commonly used and commercially available high precision drop shape analysis tool, namely the DSA100 from Krüss GmbH, was used to perform all surface tension measurements. The surface tension is determined by the software "DSA4" in accordance with DIN 55660-1. All measurements were performed at room temperature which is in the range between 22° C. and 24° C. The standard operating procedure includes the determination of the surface tension of each formulation using a fresh disposable drop dispensing system (syringe and needle). Each drop is measured over the duration of one minute with sixty measurements which are later on averaged. For each formulation three drops are measured. The final value is averaged over said measurements. The tool is regularly cross-checked against various liquids having well known surface tension.

Preferably, the formulation has a viscosity in the range from 0.8 to 50 mPas, more preferably in the range from 1 to 40 mPas, more preferably in the range from 2 to 20 mPas and most preferably in the range from 2 to 10 mPas.

The viscosity of the formulations of the present invention is measured with a 1° cone-plate rotational rheometer of the type Haake MARS III Rheometer (Thermo Scientific). The equipment allows a precise control of the temperature and sheer rate. The measurement of the viscosity is carried out at a temperature of 23.4° C. (+/−0.2° C.) and a sheer rate of 500 s$^{-1}$. Each sample is measured three times and the obtained measured values are averaged. The measurement and processing of data is carried out using the software "Haake RheoWin Job Manager" according to DIN 1342-2. The Haake MARS III Rheometer is regularly calibrated by Thermo Scientific and the tool received a certified standard factory calibration before first use.

Preferably, the content of the ester solvent according to General Formulae (I) or (II) is in the range from 0.01 to 99.99 vol.-%, more preferably from 1 to 95 vol.-%, still more preferably from 10 to 90 vol.-% and most preferably from 20 to 80 vol.-%, based on the total amount of solvents in the formulation.

The formulation may further comprise at least one additional solvent which is different from the ester solvent. Suitable additional solvents are preferably solvents which include inter alia alcohols, aldehydes, ketones, ethers, esters, amides such as $(C_{1-2}\text{-alkyl})_2\text{NH—CO—H}$, sulfur compounds, nitro compounds, hydrocarbons, halogenated hydrocarbons (e.g. chlorinated hydrocarbons), aromatic or heteroaromatic hydrocarbons and halogenated aromatic or heteroaromatic hydrocarbons.

Preferably, the further solvent is selected from the group consisting of substituted and non-substituted aromatic or linear esters such as ethyl benzoate, butyl benzoate; substituted and non-substituted aromatic or linear ethers such as 3-phenoxytoluene or anisole derivatives; substituted or non-substituted arene derivatives such as xylene; indane derivatives such as hexamethylindane; substituted and non-substituted aromatic or linear ketones; substituted and non-substituted heterocycles such as pyrrolidinones, pyridines; fluorinated or chlorinated hydrocarbons; and linear or cyclic siloxanes.

Particularly preferred additional solvents are, for example, 1,2,3,4-tetramethylbenzene, 1,2,3,5-tetramethylbenzene, 1,2,3-trimethylbenzene, 1,2,4,5-tetramethylbenzene, 1,2,4-trichlorobenzene, 1,2,4-trimethylbenzene, 1,2-dihydronaphthalene, 1,2-dimethylnaphthalene, 1,3-benzodioxolane, 1,3-diisopropylbenzene, 1,3-dimethylnaphthalene, 1,4-benzodioxane, 1,4-diisopropylbenzene, 1,4-dimethylnaphthalene, 1,5-dimethyltetralin, 1-benzothiophene, 1-bromonaphthalene, 1-chloromethylnaphthalene, 1-ethylnaphthalene, 1-methoxynaphthalene, 1-methylnaphthalene, 1-methylindole, 2,3-benzofuran, 2,3-dihydrobenzofuran, 2,3-dimethylanisole, 2,4-dimethylanisole, 2,5-dimethylanisole, 2,6-dimethylanisole, 2,6-dimethylnaphthalene, 2-bromo-3-bromomethylnaphthalene, 2-bromomethylnaphthalene, 2-bromonaphthalene, 2-ethoxynaphthalene, 2-ethylnaphthalene, 2-isopropylanisole, 2-methylanisole, 2-methylindole, 3,4-dimethylanisole, 3,5-dimethylanisole, 3-bromoquinoline, 3-methylanisole, 4-methylanisole, 5-decanolide, 5-methoxyindane, 5-methoxyindole, 5-tert-butyl-m-xylene, 6-methylquinoline, 8-methylquinoline, acetophenone, anisole, benzonitrile, benzothiazole, benzyl acetate, bromobenzene, butyl benzoate, butyl phenyl ether, cyclohexylbenzene, decahydronaphthol, dimethoxytoluene, 3-phenoxytoluene, diphenyl ether, propiophenone, ethylbenzene, ethyl benzoate, γ-terpinene, hexylbenzene, indane, hexamethylindane, indene, isochroman, cumene, m-cymene, mesitylene, methyl benzoate, o-, m-, p-xylene, propyl benzoate, propylbenzene, o-dichlorobenzene, pentylbenzene, phenetol, ethoxybenzene, phenyl acetate, p-cymene, propiophenone, secbutylbenzene, t-butylbenzene, thiophene, toluene, veratrol, monochlorobenzene, o-dichlorobenzene, pyridine, pyrazine, pyrimidine, pyrrolidinone, morpholine, dimethylacetamide, dimethyl sulfoxide, decaline and/or mixtures of these compounds.

These solvents can be employed individually or as a mixture of two, three or more solvents forming the additional solvent.

The content of the organic functional material in the formulation is preferably in the range from 0.001 to 20 weight-%, preferably in the range from 0.01 to 10 weight-% and more preferably in the range from 0.1 to 5 weight-%, based on the total weight of the formulation.

The formulation of the present invention comprises at least one organic functional material which can be employed for the production of functional layers of electronic devices. Organic functional materials are generally the organic materials which are introduced between the anode and the cathode of an electronic device.

The organic functional material is selected from the group consisting of organic conductors, organic semiconductors, organic fluorescent compounds, organic phosphorescent compounds, organic light-absorbent compounds, organic light-sensitive compounds, organic photosensitisation agents and other organic photoactive compounds, selected from organometallic complexes of transition metals, rare earths, lanthanides and actinides.

Preferably, the organic functional material is selected from the group consisting of fluorescent emitters, phosphorescent emitters, host materials, matrix materials, exciton-blocking materials, electron-transport materials, electron-injection materials, hole-conductor materials, hole-injection materials, n-dopants, p-dopants, wide-band-gap materials, electron-blocking materials and hole-blocking materials.

Preferred embodiments of organic functional materials are disclosed in detail in WO 2011/076314 A1 which is incorporated into the present application by way of reference.

In a preferred embodiment, the organic functional material is selected from the group consisting of fluorescent emitters and phosphorescent emitters.

The organic functional material can be a compound having a low molecular weight, a polymer, an oligomer or a dendrimer, where the organic functional material may also be in the form of a mixture. In a preferred embodiment the formulations according to the invention may comprise two different organic functional materials having a low molecular weight, one compound having a low molecular weight and one polymer or two polymers (blend). In a further preferred embodiment the formulations according to the invention may comprise up to five different organic functional materials which are selected from compounds having a low molecular weight or from polymers.

Preferably, the organic functional material has a low molecular weight. A low molecular weight is a weight of ≤3,000 g/mol, particularly preferably ≤2,000 g/mol and especially preferably ≤1,800 g/mol.

Organic functional materials are frequently described by the properties of their frontier orbitals, which are described in greater detail below. Molecular orbitals, in particular also the highest occupied molecular orbital (HOMO) and the lowest unoccupied molecular orbital (LUMO), their energy levels and the energy of the lowest triplet state $T_1$ or of the lowest excited singlet state $S_1$ of the materials are determined via quantum-chemical calculations. In order to calculate organic substances without metals, firstly a geometry optimisation is carried out using the "Ground State/Semi-empirical/Default Spin/AM1/Charge 0/Spin Singlet" method. An energy calculation is subsequently carried out on the basis of the optimised geometry. The "TD-SCF/DFT/Default Spin/B3PW91" method with the "6-31G(d)" base set (charge 0, spin singlet) is used here. For metal-containing compounds, the geometry is optimised via the "Ground State/Hartree-Fock/Default Spin/LanL2 MB/Charge 0/Spin Singlet" method. The energy calculation is carried out analogously to the above-described method for the organic substances, with the difference that the "LanL2DZ" base set is used for the metal atom and the "6-31G(d)" base set is used for the ligands. The energy calculation gives the HOMO energy level HEh or LUMO energy level LEh in hartree units. The HOMO and LUMO energy levels in electron volts calibrated with reference to cyclic voltammetry measurements are determined therefrom as follows:

$$HOMO(eV)=((HEh*27.212)-0.9899)/1.1206$$

$$LUMO(eV)=((LEh*27.212)-2.0041)/1.385$$

For the purposes of this application, these values are to be regarded as HOMO and LUMO energy levels respectively of the materials.

The lowest triplet state $T_1$ is defined as the energy of the triplet state having the lowest energy which arises from the quantum-chemical calculation described.

The lowest excited singlet state $S_1$ is defined as the energy of the excited singlet state having the lowest energy which arises from the quantum-chemical calculation described.

The method described herein is independent of the software package used and always gives the same results. Examples of frequently used programs for this purpose are "Gaussian09 W" (Gaussian Inc.) and Q-Chem 4.1 (Q-Chem, Inc.).

Materials having hole-injection properties, also called hole-injection materials herein, simplify or facilitate the transfer of holes, i.e. positive charges, from the anode into an organic layer. In general, a hole-injection material has an HOMO level which is in the region of or above the Fermi level of the anode.

Compounds having hole-transport properties, also called hole-transport materials herein, are capable of transporting holes, i.e. positive charges, which are generally injected from the anode or an adjacent layer, for example a hole-injection layer. A hole-transport material generally has a high HOMO level of preferably at least −5.4 eV. Depending on the structure of an electronic device, it may also be possible to employ a hole-transport material as hole-injection material.

The preferred compounds which have hole-injection and/or hole-transport properties include, for example, triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, pyrrole and furan derivatives and further O-, S- or N-containing heterocycles having a high HOMO (HOMO=highest occupied molecular orbital). Polymers such as PEDOT:PSS can also be used as compounds with hole-injection and/or hole-transport properties.

As compounds which have hole-injection and/or hole-transport properties, particular mention may be made of phenylenediamine derivatives (U.S. Pat. No. 3,615,404), arylamine derivatives (U.S. Pat. No. 3,567,450), amino-substituted chalcone derivatives (U.S. Pat. No. 3,526,501), styrylanthracene derivatives (JP-A-56-46234), polycyclic aromatic compounds (EP 1009041), polyarylalkane derivatives (U.S. Pat. No. 3,615,402), fluorenone derivatives (JP-A-54-110837), hydrazone derivatives (U.S. Pat. No. 3,717,462), acylhydrazones, stilbene derivatives (JP-A61-210363), silazane derivatives (U.S. Pat. No. 4,950,950), polysilanes (JP-A-2-204996), aniline copolymers (JP-A-2-282263), thiophene oligomers (JP Heisei 1 (1989) 211399), polythiophenes, poly(N-vinylcarbazole) (PVK), polypyrroles, polyanilines and other electrically conducting macromolecules, porphyrin compounds (JP-A-63-2956965, U.S. Pat. No. 4,720,432), aromatic dimethylidene-type compounds, carbazole compounds, such as, for example, CDBP, CBP, mCP, aromatic tertiary amine and styrylamine compounds (U.S. Pat. No. 4,127,412), such as, for example, triphenylamines of the benzidine type, triphenylamines of the styrylamine type and triphenylamines of the diamine type. It is also possible to use arylamine dendrimers (JP Heisei 8 (1996) 193191), monomeric triarylamines (U.S. Pat. No. 3,180,730), triarylamines containing one or more vinyl radicals and/or at least one functional group containing active hydrogen (U.S. Pat. Nos. 3,567,450 and 3,658,520), or tetraaryldiamines (the two tertiary amine units are connected via an aryl group). More triarylamino groups may also be present in the molecule. Phthalocyanine derivatives, naphthalocyanine derivatives, butadiene derivatives and quinoline derivatives, such as, for example, dipyrazino[2,3-f:2',3'-h]-quinoxalinehexacarbonitrile, are also suitable.

Preference is given to aromatic tertiary amines containing at least two tertiary amine units (US 2008/0102311 A1, U.S. Pat. Nos. 4,720,432 and 5,061,569), such as, for example, NPD (α-NPD=4,4'-bis[N-(1-naphthyl)-N-phenylamino]biphenyl) (U.S. Pat. No. 5,061,569), TPD 232 (=N,N'-bis-(N,N'-diphenyl-4-aminophenyl)-N,N-diphenyl-4,4'-diamino-1,1'-biphenyl) or MTDATA (MTDATA or m-MTDATA=4,4',4"-tris[3-methylphenyl)phenylamino]-triphenylamine) (JP-A-4-308688), TBDB (=N,N,N',N'-tetra(4-biphenyl)diaminobiphenylene), TAPC (=1,1-bis(4-di-p-tolylaminophenyl)cyclohexane), TAPPP (=1,1-bis(4-di-p-tolylaminophenyl)-3-phenylpropane), BDTAPVB (=1,4-bis[2-[4-[N,N-di(p-tolyl)amino]phenyl]vinyl]benzene), TTB (=N,N,N',N'-tetra-p-tolyl-4,4'-diaminobiphenyl), TPD (=4,4'-bis[N-3-methylphenyl]-N-phenylamino)biphenyl), N,N,N',N'-tetraphenyl-4,4'-diamino-1,1',4',1",4",1'''-quaterphenyl, likewise tertiary amines containing carbazole units, such as, for example, TCTA (=4-(9H-carbazol-9-yl)-N,N-bis[4-(9H-carbazol-9-yl)phenyl]benzenamine). Preference is likewise given to hexaazatriphenylene compounds in accordance with US 2007/0092755 A1 and phthalocyanine derivatives (for example $H_2Pc$, CuPc (=copper phthalocyanine), CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O—GaPc).

Particular preference is given to the following triarylamine compounds of the formulae (TA-1) to (TA-12), which are disclosed in the documents EP 1162193 B1, EP 650 955 B1, Synth. Metals 1997, 91(1-3), 209, DE 19646119 A1, WO 2006/122630 A1, EP 1 860 097 A1, EP 1834945 A1, JP 08053397 A, U.S. Pat. No. 6,251,531 B1, US 2005/0221124, JP 08292586 A, U.S. Pat. No. 7,399,537 B2, US 2006/0061265 A1, EP 1 661 888 and WO 2009/041635. The said compounds of the formulae (TA-1) to (TA-12) may also be substituted:

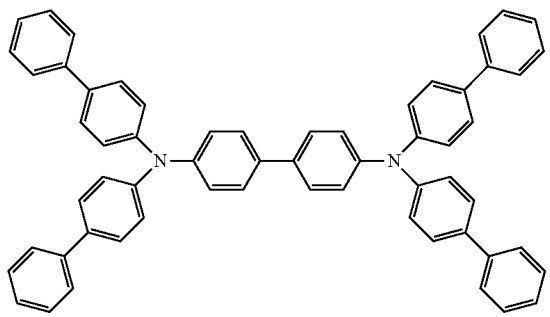

formula TA-1

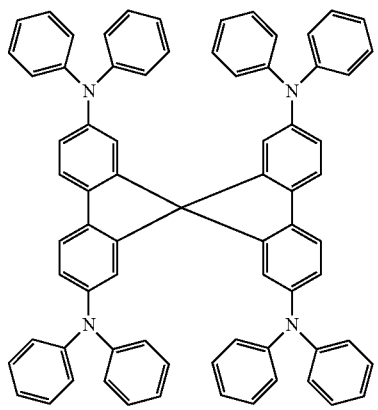

formula TA-2

-continued
formula TA-3
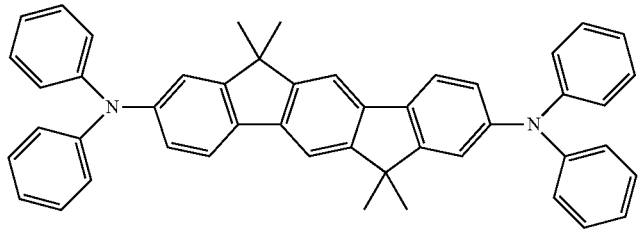
formula TA-4
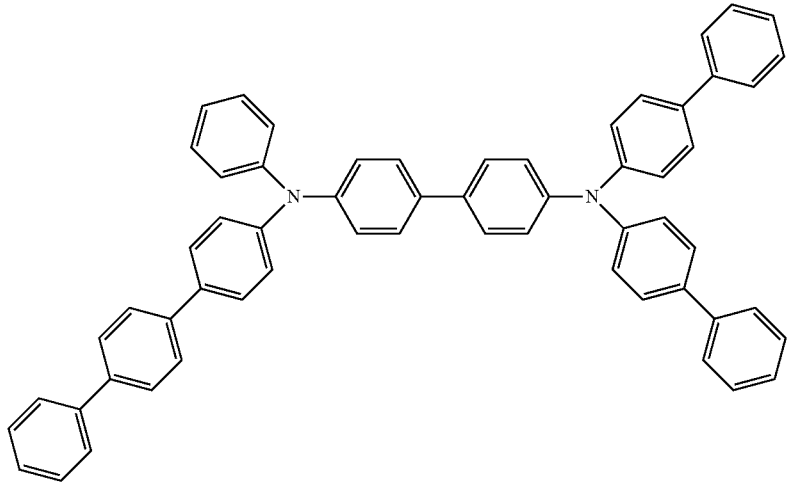
formula TA-5
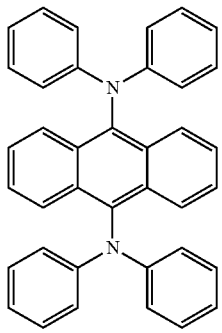
formula TA-6
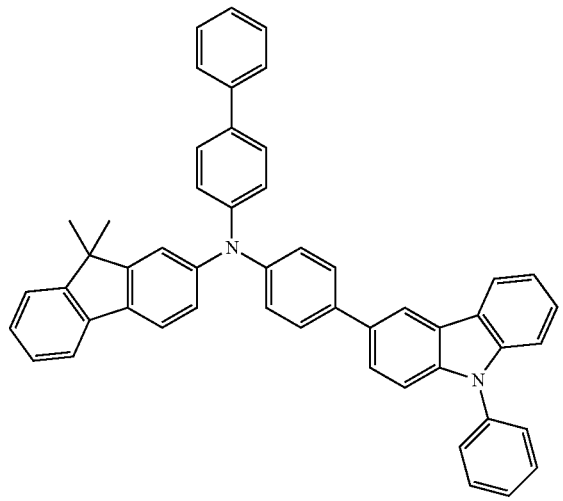
formula TA-7
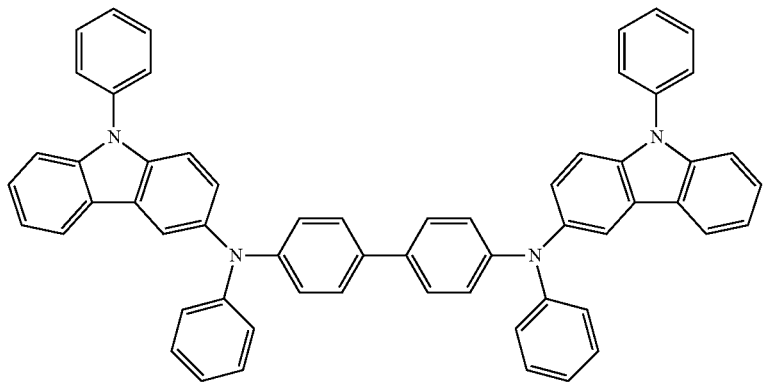

-continued
formula TA-8
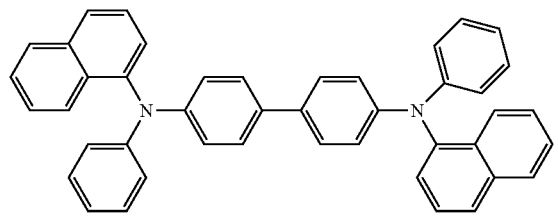
NPB = alpha-NPD
formula TA-9
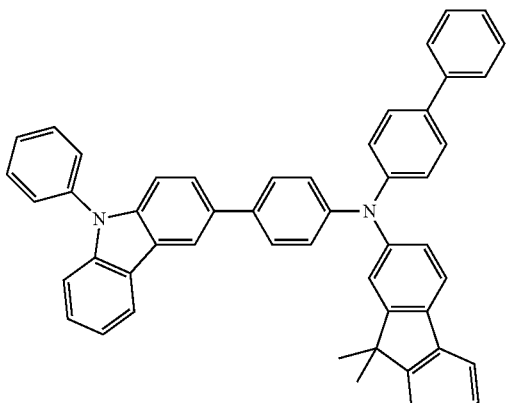
formula TA-10
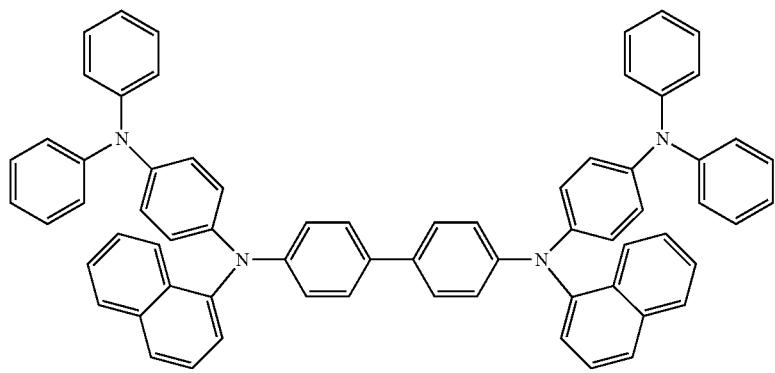
formula TA-11
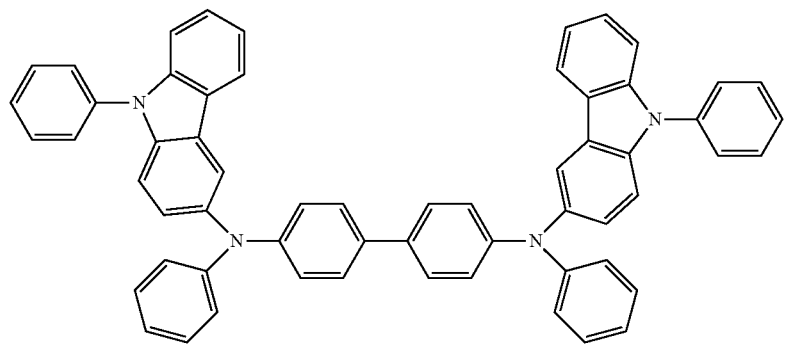
formula TA-12
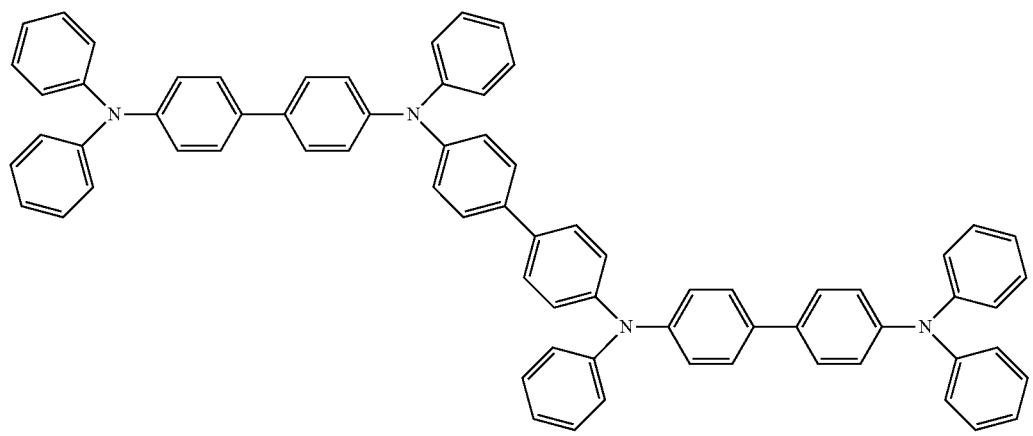

Further compounds which can be employed as hole-injection materials are described in EP 0891121 A1 and EP 1029909 A1, injection layers in general in US 2004/0174116 A1.

These arylamines and heterocycles which are generally employed as hole-injection and/or hole-transport materials preferably result in an HOMO in the polymer of greater than −5.8 eV (vs. vacuum level), particularly preferably greater than −5.5 eV.

Compounds which have electron-injection and/or electron-transport properties are, for example, pyridine, pyrimidine, pyridazine, pyrazine, oxadiazole, quinoline, quinoxaline, anthracene, benzanthracene, pyrene, perylene, benzimidazole, triazine, ketone, phosphine oxide and phenazine derivatives, but also triarylboranes and further O-, S- or N-containing heterocycles having a low LUMO (LUMO=lowest unoccupied molecular orbital).

Particularly suitable compounds for electron-transporting and electron-injecting layers are metal chelates of 8-hydroxyquinoline (for example LiQ, AlQ$_3$, GaQ$_3$, MgQ$_2$, ZnQ$_2$, InQ$_3$, ZrQ$_4$), BAlQ, Ga oxinoid complexes, 4-azaphenanthren-5-ol-Be complexes (U.S. Pat. No. 5,529,853 A, cf. formula ET-1), butadiene derivatives (U.S. Pat. No. 4,356,429), heterocyclic optical brighteners (U.S. Pat. No. 4,539,507), benzimidazole derivatives (US 2007/0273272 A1), such as, for example, TPBI (U.S. Pat. No. 5,766,779, cf. formula ET-2), 1,3,5-triazines, for example spirobifluorenyltriazine derivatives (for example in accordance with DE 102008064200), pyrenes, anthracenes, tetracenes, fluorenes, spirofluorenes, dendrimers, tetracenes (for example rubrene derivatives), 1,10-phenanthroline derivatives (JP 2003-115387, JP 2004-311184, JP-2001, 267080, WO 02/043449), silacyclopentadiene derivatives (EP 1480280, EP 1478032, EP 1469533), borane derivatives, such as, for example, triarylborane derivatives containing Si (US 2007/0087219 A1, cf. formula ET-3), pyridine derivatives (JP 2004-200162), phenanthrolines, especially 1,10-phenanthroline derivatives, such as, for example, BCP and Bphen, also several phenanthrolines connected via biphenyl or other aromatic groups (US-2007-0252517 A1) or phenanthrolines connected to anthracene (US 2007-0122656 A1, cf. formulae ET-4 and ET-5).

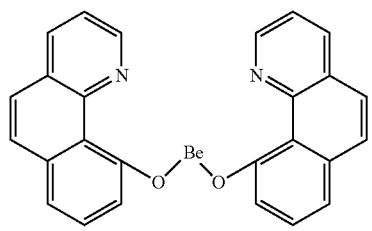

formula ET-1

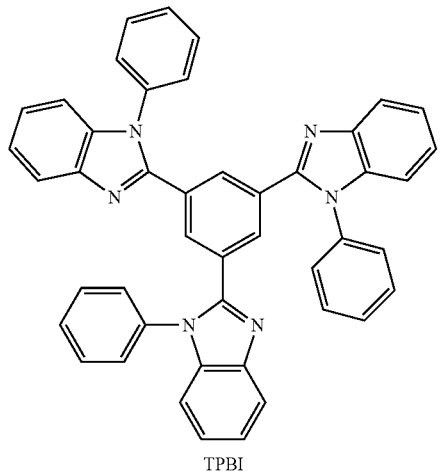

TPBI 2,2′,2″-(1,3,5-benzenetriyl)tris(1-phenyl-1H-benzimidazole)

formula ET-2

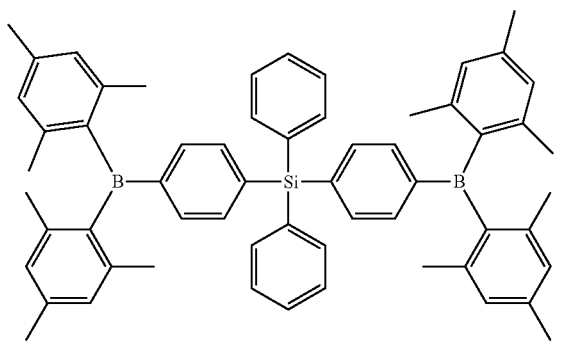

formula ET-3

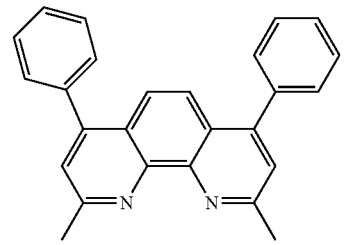

formula ET-4

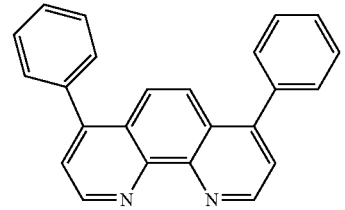

formula ET-5

Likewise suitable are heterocyclic organic compounds, such as, for example, thiopyran dioxides, oxazoles, triazoles, imidazoles or oxadiazoles. Examples of the use of five-membered rings containing N, such as, for example, oxazoles, preferably 1,3,4-oxadiazoles, for example compounds of the formulae ET-6, ET-7, ET-8 and ET-9, which are disclose, inter alia, in US 2007/0273272 A1; thiazoles, oxadiazoles, thiadiazoles, triazoles, inter alia, see US 2008/0102311 A1 and Y. A. Levin, M. S. Skorobogatova, Khimiya Geterotsiklicheskikh Soedinenii 1967 (2), 339-341, preferably compounds of the formula ET-10, silacyclopentadiene derivatives. Preferred compounds are the following of the formulae (ET-6) to (ET-10):

formula ET-6

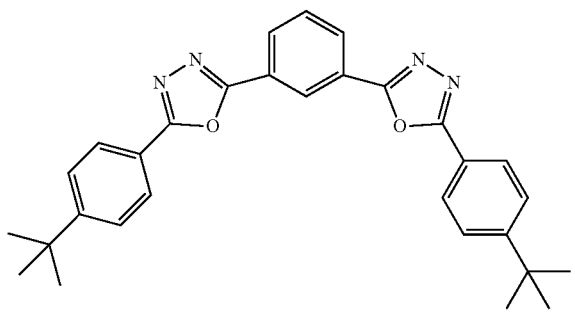

formula ET-7

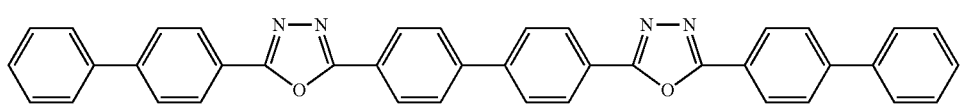

formula ET-8

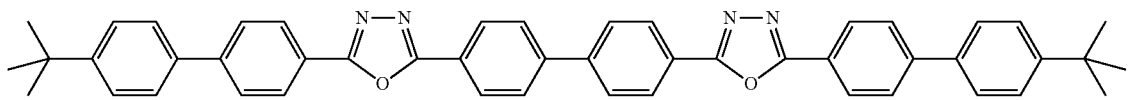

formula ET-9

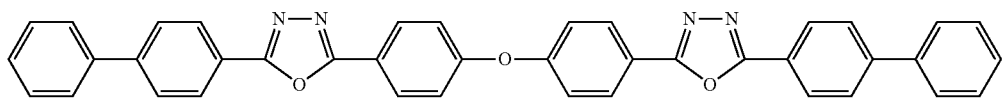

formula ET-10

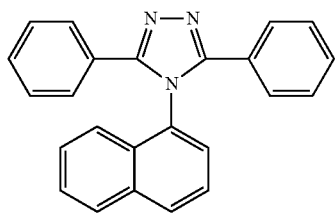

It is also possible to employ organic compounds, such as derivatives of fluorenone, fluorenylidenemethane, perylenetetracarbonic acid, anthraquinonedimethane, diphenoquinone, anthrone and anthraquinonediethylenediamine.

Preference is given to 2,9,10-substituted anthracenes (with 1- or 2-naphthyl and 4- or 3-biphenyl) or molecules which contain two anthracene units (US2008/0193796 A1, cf. formula ET-11). Also very advantageous is the connection of 9,10-substituted anthracene units to benzimidazole derivatives (US 2006 147747 A and EP 1551206 A1, cf. formulae ET-12 and ET-13).

formula ET-11

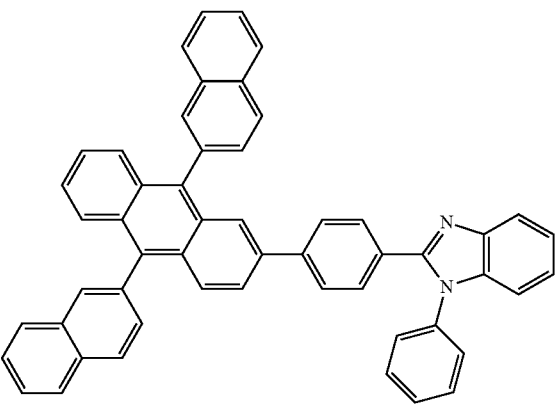

-continued formula ET-12

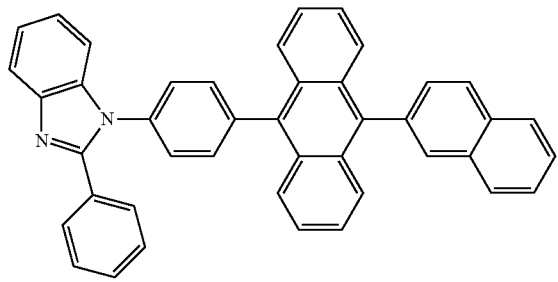

formula ET-13

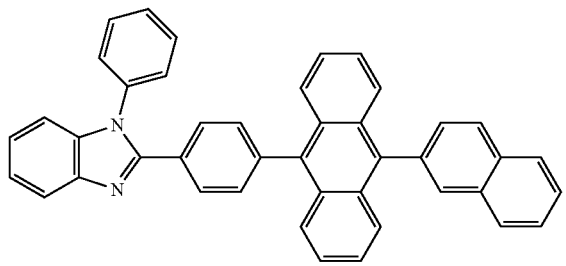

The compounds which are able to generate electron-injection and/or electron-transport properties preferably result in an LUMO of less than −2.5 eV (vs. vacuum level), particularly preferably less than −2.7 eV.

n-Dopants herein are taken to mean reducing agents, i.e. electron donors. Preferred examples of n-dopants are W(hpp)$_4$ and other electron-rich metal complexes in accordance with WO 2005/086251 A2, P=N compounds (for example WO 2012/175535 A1, WO 2012/175219 A1), naphthylenecarbodiimides (for example WO 2012/168358 A1), fluorenes (for example WO 2012/031735 A1), free radicals and diradicals (for example EP 1837926 A1, WO 2007/107306 A1), pyridines (for example EP 2452946 A1, EP 2463927 A1), N-heterocyclic compounds (for example WO 2009/000237 A1) and acridines as well as phenazines (for example US 2007/145355 A1).

The present formulations may comprise emitters. The term emitter denotes a material which, after excitation, which can take place by transfer of any type of energy, allows a radiative transition into a ground state with emission of light. In general, two classes of emitter are known, namely fluorescent and phosphorescent emitters. The term fluorescent emitter denotes materials or compounds in which a radiative transition from an excited singlet state into the ground state takes place. The term phosphorescent emitter preferably denotes luminescent materials or compounds which contain transition metals.

Emitters are frequently also called dopants if the dopants cause the properties described above in a system. A dopant in a system comprising a matrix material and a dopant is taken to mean the component whose proportion in the mixture is the smaller. Correspondingly, a matrix material in a system comprising a matrix material and a dopant is taken to mean the component whose proportion in the mixture is the greater. Accordingly, the term phosphorescent emitter can also be taken to mean, for example, phosphorescent dopants.

Compounds which are able to emit light include, inter alia, fluorescent emitters and phosphorescent emitters. These include, inter alia, compounds containing stilbene, stilbenamine, styrylamine, coumarine, rubrene, rhodamine, thiazole, thiadiazole, cyanine, thiophene, paraphenylene, perylene, phtalocyanine, porphyrin, ketone, quinoline, imine, anthracene and/or pyrene structures. Particular preference is given to compounds which are able to emit light from the triplet state with high efficiency, even at room temperature, i.e. exhibit electrophosphorescence instead of electrofluorescence, which frequently causes an increase in the energy efficiency. Suitable for this purpose are firstly compounds which contain heavy atoms having an atomic number of greater than 36. Preference is given to compounds which contain d- or f-transition metals which satisfy the above-mentioned condition. Particular preference is given here to corresponding compounds which contain elements from group 8 to 10 (Ru, Os, Rh, Ir, Pd, Pt). Suitable functional compounds here are, for example, various complexes, as described, for example, in WO 02/068435 A1, WO 02/081488 A1, EP 1239526 A2 and WO 2004/026886 A2.

Preferred compounds which can serve as fluorescent emitters are described by way of example below. Preferred fluorescent emitters are selected from the class of the monostyrylamines, the distyrylamines, the tristyrylamines, the tetrastyrylamines, the styrylphosphines, the styryl ethers and the arylamines.

A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or an aromatic amine in the sense of the present invention is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 2,6- or 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Further preferred fluorescent emitters are selected from indenofluorenamines or indenofluorenediamines, which are described, inter alia, in WO 2006/122630; benzoindenofluorenamines or benzoindenofluorenediamines, which are described, inter alia, in WO 2008/006449; and dibenzoindenofluorenamines or dibenzoindenofluorenediamines, which are described, inter alia, in WO 2007/140847.

Examples of compounds from the class of the styrylamines which can be employed as fluorescent emitters are substituted or unsubstituted tristilbenamines or the dopants described in WO 2006/000388, WO 2006/058737, WO 2006/000389, WO 2007/065549 and WO 2007/115610. Distyrylbenzene and distyrylbiphenyl derivatives are described in U.S. Pat. No. 5,121,029. Further styrylamines can be found in US 2007/0122656 A1.

Particularly preferred styrylamine compounds are the compounds of the formula EM-1 described in U.S. Pat. No. 7,250,532 B2 and the compounds of the formula EM-2 described in DE 10 2005 058557 A1:

formula EM-1

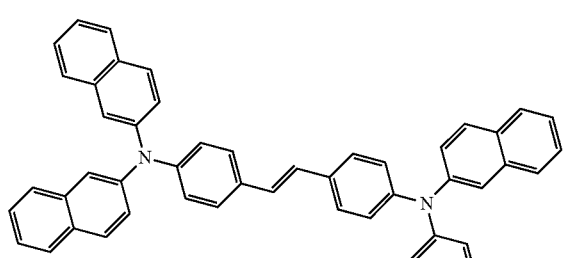

formula EM-2

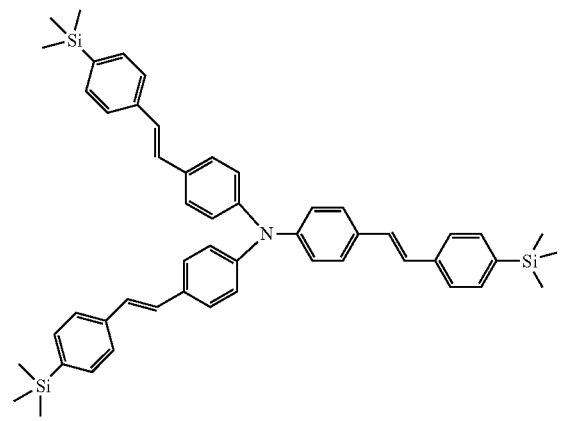

Particularly preferred triarylamine compounds are compounds of the formulae EM-3 to EM-15 disclosed in CN 1583691 A, JP 08/053397 A and U.S. Pat. No. 6,251,531 B1, EP 1957606 A1, US 2008/0113101 A1, US 2006/210830 A, WO 2008/006449 and DE 102008035413 derivatives thereof:

formula EM-3

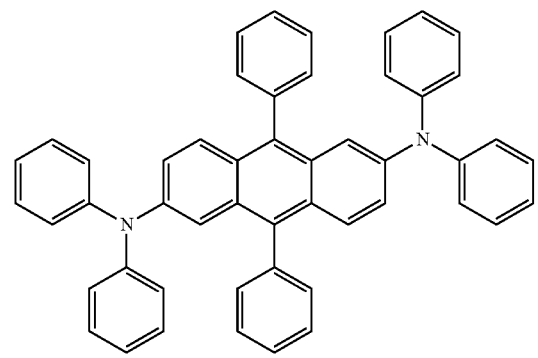

formula EM-4

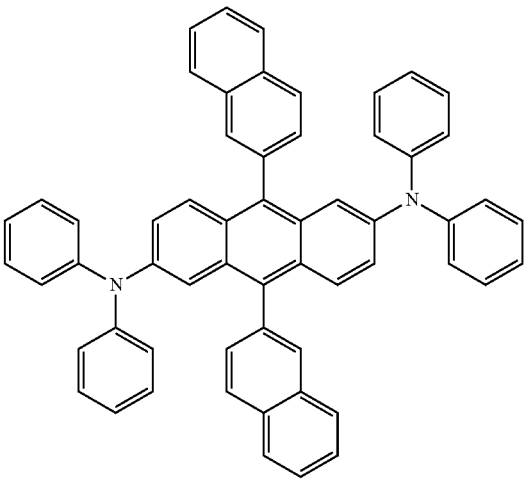

formula EM-5

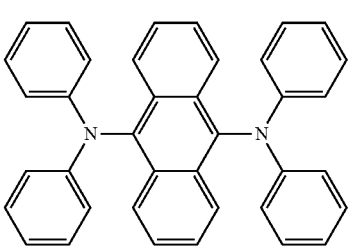

formula EM-6

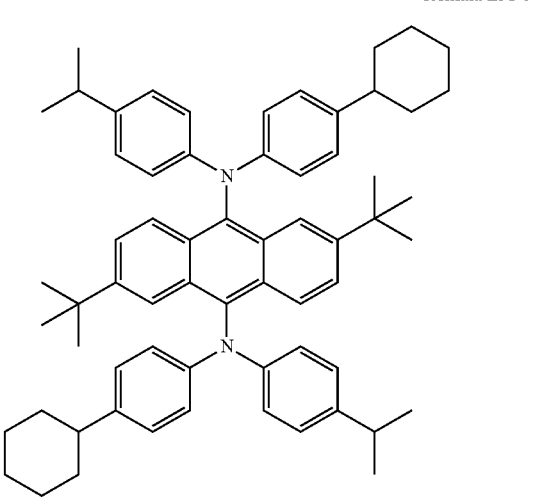

formula EM-7

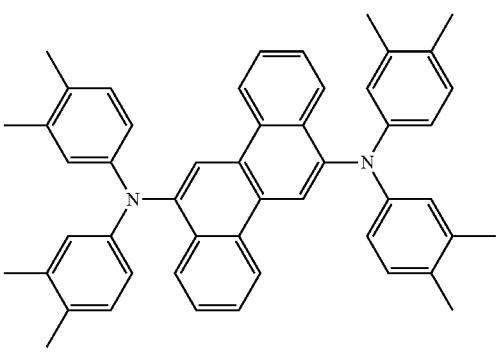

-continued formula EM-8

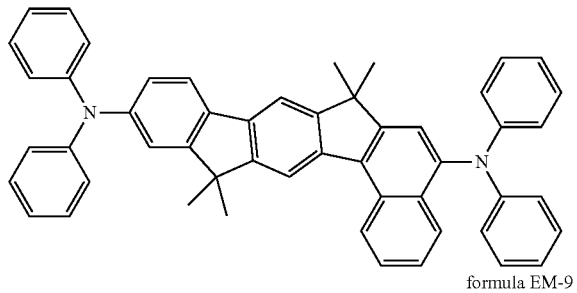

formula EM-9

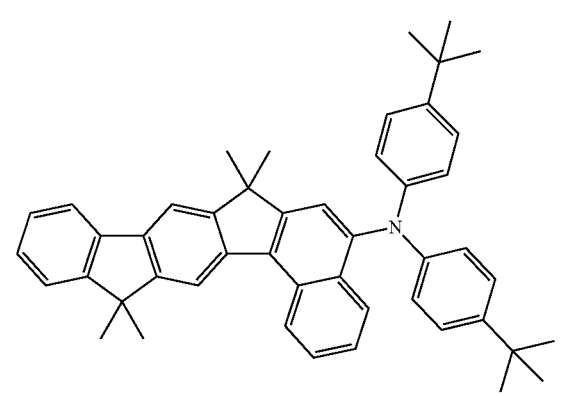

formula EM-10

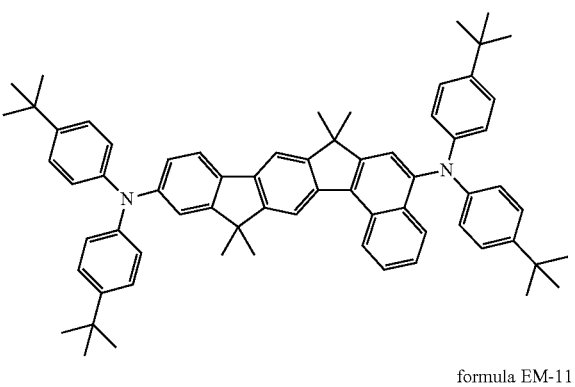

formula EM-11

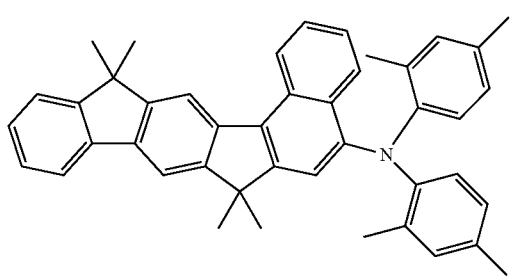

formula EM-12

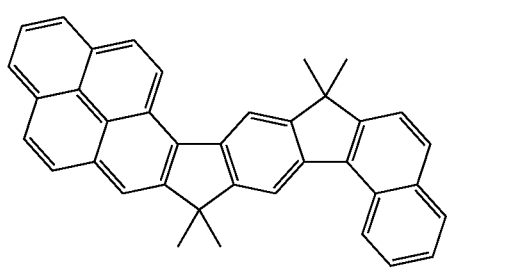

-continued formula EM-13

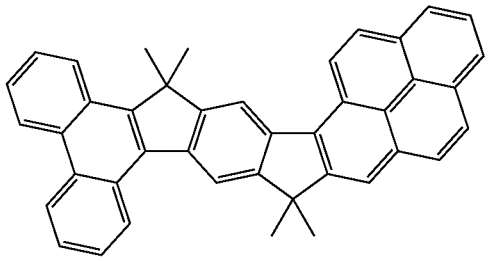

formula EM-14

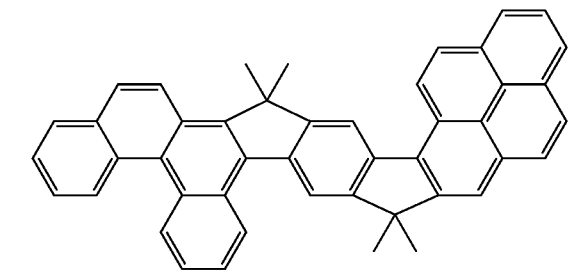

formula EM-15

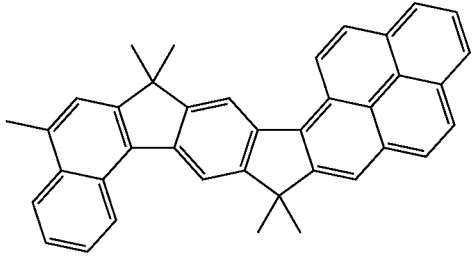

Further preferred compounds which can be employed as fluorescent emitters are selected from derivatives of naphthalene, anthracene, tetracene, benzanthracene, benzophenanthrene (DE 10 2009 005746), fluorene, fluoranthene, periflanthene, indenoperylene, phenanthrene, perylene (US 2007/0252517 A1), pyrene, chrysene, decacyclene, coronene, tetraphenylcyclopentadiene, pentaphenylcyclopentadiene, fluorene, spirofluorene, rubrene, coumarine (U.S. Pat. Nos. 4,769,292, 6,020,078, US 2007/0252517 A1), pyran, oxazole, benzoxazole, benzothiazole, benzimidazole, pyrazine, cinnamic acid esters, diketopyrrolopyrrole, acridone and quinacridone (US 2007/0252517 A1).

Of the anthracene compounds, particular preference is given to 9,10-substituted anthracenes, such as, for example, 9,10-diphenylanthracene and 9,10-bis(phenylethynyl)anthracene. 1,4-Bis(9'-ethynylanthracenyl)benzene is also a preferred dopant.

Preference is likewise given to derivatives of rubrene, coumarine, rhodamine, quinacridone, such as, for example, DMQA (=N,N'-dimethylquinacridone), dicyanomethylenepyran, such as, for example, DCM (=4-(dicyanoethylene)-6-(4-dimethylaminostyryl-2-methyl)-4H-pyran), thiopyran, polymethine, pyrylium and thiapyrylium salts, periflanthene and indenoperylene.

Blue fluorescent emitters are preferably polyaromatic compounds, such as, for example, 9,10-di(2-naphthylanthracene) and other anthracene derivatives, derivatives of tetracene, xanthene, perylene, such as, for example, 2,5,8,11-tetra-t-butylperylene, phenylene, for example 4,4'-bis(9-ethyl-3-carbazovinylene)-1,1'-biphenyl, fluorene, fluoranthene, arylpyrenes (US 2006/0222886 A1), arylenevinylenes (U.S. Pat. Nos. 5,121,029, 5,130,603), bis(azinyl)imine-boron compounds (US 2007/0092753 A1), bis(azinyl)methene compounds and carbostyryl compounds.

Further preferred blue fluorescent emitters are described in C. H. Chen et al.: "Recent developments in organic electroluminescent materials" Macromol. Symp. 125, (1997) 1-48 and "Recent progress of molecular organic electroluminescent materials and devices" Mat. Sci. and Eng. R, 39 (2002), 143-222.

Further preferred blue-fluorescent emitters are the hydrocarbons disclosed in DE 102008035413.

Preferred compounds which can serve as phosphorescent emitters are described below by way of example.

Examples of phosphorescent emitters are revealed by WO 00/70655, WO 01/41512, WO 02/02714, WO 02/15645, EP 1191613, EP 1191612, EP 1191614 and WO 2005/033244. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

Phosphorescent metal complexes preferably contain Ir, Ru, Pd, Pt, Os or Re.

Preferred ligands are 2-phenylpyridine derivatives, 7,8-benzoquinoline derivatives, 2-(2-thienyl)pyridine derivatives, 2-(1-naphthyl)pyridine derivatives, 1-phenylisoquinoline derivatives, 3-phenylisoquinoline derivatives or 2-phenylquinoline derivatives. All these compounds may be substituted, for example by fluoro, cyano and/or trifluoromethyl substituents for blue. Auxiliary ligands are preferably acetylacetonate or picolinic acid.

In particular, complexes of Pt or Pd with tetradentate ligands of the formula EM-16 are suitable

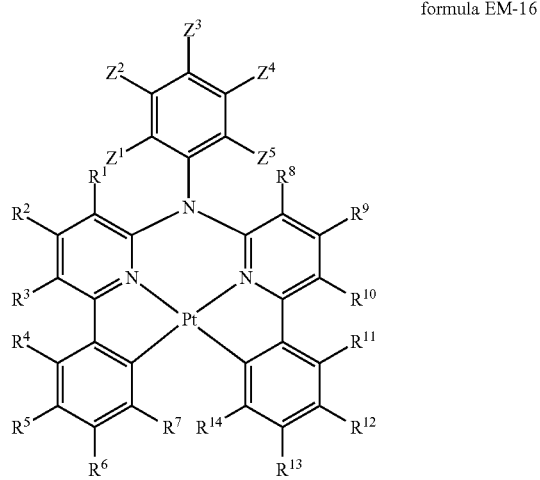

formula EM-16

The compounds of the formula EM-16 are described in greater detail in US 2007/0087219 A1, where, for an explanation of the substituents and indices in the above formula, reference is made to this specification for disclosure purposes. Furthermore, Pt-porphyrin complexes having an enlarged ring system (US 2009/0061681 A1) and Ir complexes, for example 2,3,7,8,12,13,17,18-octaethyl-21H, 23H-porphyrin-Pt(II), tetraphenyl-Pt(II) tetrabenzoporphyrin (US 2009/0061681 A1), cis-bis(2-phenylpyridinatoN, $C^{2'}$)Pt(II), cis-bis(2-(2'-thienyl)pyridinato-N,$C^{3'}$)Pt(II), cis-bis(2-(2'-thienyl)quinolinato-N,$C^{5'}$)Pt(II), (2-(4,6-difluorophenyl)pyridinato-N,$C^{2'}$)Pt(II) (acetylacetonate), or tris(2-phenylpyridinato-N,$C^{2'}$)Ir(III) (=Ir(ppy)$_3$, green), bis (2-phenylpyridinato-N,$C^2$) Ir(II) (acetylacetonate) (=Ir (ppy)$_2$ acetylacetonate, green, US 2001/0053462 A1, Baldo, Thompson et al. Nature 403, (2000), 750-753), bis(1-phenylisoquinolinato-N,$C^{2'}$)(2-phenylpyridinato-N,$C^{2'}$)iridium (III), bis(2-phenylpyridinato-N,$C^{2'}$)(1-phenylisoquinolinato-N,$C^{2'}$)iridium(III), bis(2-(2'-benzothienyl)pyridinato-N,$C^{3'}$)iridium(III) (acetylacetonate), bis(2-(4',6'-difluorophenyl)pyridinato-N,$C^{2'}$)iridium(III) (piccolinate) (FIrpic, blue), bis(2-(4',6'-difluorophenyl)pyridinato-N,$C^{2'}$) Ir(III) (tetrakis(1-pyrazolyl)borate), tris(2-(biphenyl-3-yl)-4-tert-butylpyridine)iridium(III), (ppz)$_2$Ir(5phdpym) (US 2009/0061681 A1), (45ooppz)$_2$-Ir(5phdpym) (US 2009/0061681 A1), derivatives of 2-phenylpyridine-Ir complexes, such as, for example, PQIr (=iridium(III) bis(2-phenylquinolylN,$C^{2'}$)acetylacetonate), tris(2-phenylisoquinolinato-N, C)Ir(1 II) (red), bis(2-(2'-benzo[4,5-a]thienyl)pyridinato-N, $C^3$) Ir (acetylacetonate) ([Btp$_2$Ir(acac)], red, Adachi et al. Appl. Phys. Lett. 78 (2001), 1622-1624).

Likewise suitable are complexes of trivalent lanthanides, such as, for example, Tb$^{3+}$ and Eu$^{3+}$ (J. Kido et al. Appl. Phys. Lett. 65 (1994), 2124, Kido et al. Chem. Lett. 657, 1990, US 2007/0252517 A1), or phosphorescent complexes of Pt(II), Ir(I), Rh(I) with maleonitrile dithiolate (Johnson et al., JACS 105, 1983, 1795), Re(I) tricarbonyl-diimine complexes (Wrighton, JACS 96, 1974, 998, inter alia), Os(II) complexes with cyano ligands and bipyridyl or phenanthroline ligands (Ma et al., Synth. Metals 94, 1998, 245).

Further phosphorescent emitters having tridentate ligands are described in U.S. Pat. No. 6,824,895 and U.S. Ser. No. 10/729,238. Red-emitting phosphorescent complexes are found in U.S. Pat. Nos. 6,835,469 and 6,830,828.

Particularly preferred compounds which are used as phosphorescent dopants are, inter alia, the compounds of the formula EM-17 described, inter alia, in US 2001/0053462 A1 and Inorg. Chem. 2001, 40(7), 1704-1711, JACS 2001, 123(18), 4304-4312, and derivatives thereof.

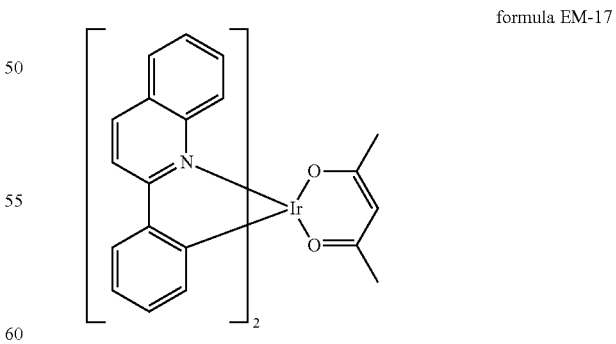

formula EM-17

Derivatives are described in U.S. Pat. No. 7,378,162 B2, U.S. Pat. No. 6,835,469 B2 and JP 2003/253145 A.

Furthermore, the compounds of the formulae EM-18 to EM-21 described in U.S. Pat. No. 7,238,437 B2, US 2009/008607 A1 and EP 1348711, and derivatives thereof, can be employed as emitters.

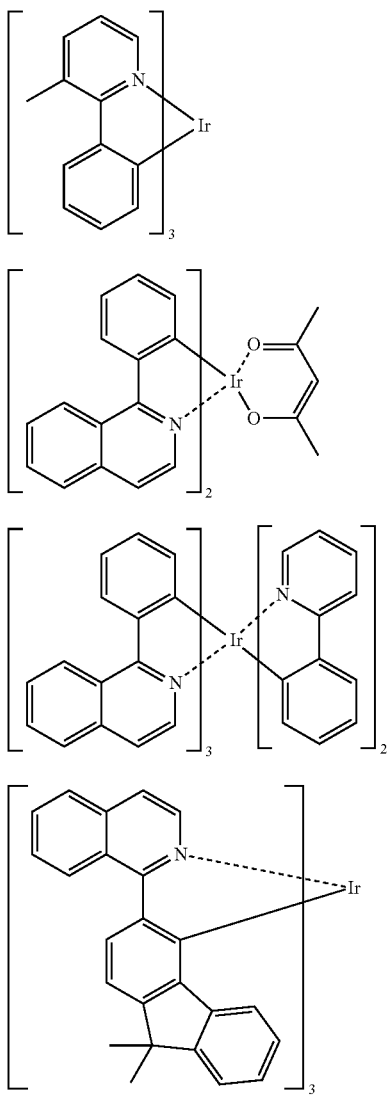

formula EM-18 formula EM-19 formula EM-20 formula EM-21

Quantum dots can likewise be employed as emitters, these materials being disclosed in detail in WO 2011/076314 A1.

Compounds which are employed as host materials, in particular together with emitting compounds, include materials from various classes of substance.

Host materials generally have larger band gaps between HOMO and LUMO than the emitter materials employed. In addition, preferred host materials exhibit properties of either a hole- or electron-transport material. Furthermore, host materials can have both electron- and hole-transport properties.

Host materials are in some cases also called matrix material, in particular if the host material is employed in combination with a phosphorescent emitter in an OLED.

Preferred host materials or co-host materials, which are employed, in particular, together with fluorescent dopants, are selected from the classes of the oligoarylenes (for example 2,2',7,7'-tetraphenylspirobifluorene in accordance with EP 676461 or dinaphthylanthracene), in particular the oligoarylenes containing condensed aromatic groups, such as, for example, anthracene, benzanthracene, benzophenanthrene (DE 10 2009 005746, WO 2009/069566), phenanthrene, tetracene, coronene, chrysene, fluorene, spirofluorene, perylene, phthaloperylene, naphthaloperylene, decacyclene, rubrene, the oligoarylenevinylenes (for example DPVBi=4,4'-bis(2,2-diphenylethenyl)-1,1'-biphenyl or spiro-DPVBi in accordance with EP 676461), the polypodal metal complexes (for example in accordance with WO 04/081017), in particular metal complexes of 8-hydroxyquinoline, for example AlQ$_3$ (=aluminium(III) tris(8-hydroxyquinoline)) or bis(2-methyl-8-quinolinolato)-4-(phenylphenolinolato)aluminium, also with imidazole chelate (US 2007/0092753 A1) and the quinoline-metal complexes, aminoquinoline-metal complexes, benzoquinoline-metal complexes, the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239).

Particularly preferred compounds which can serve as host materials or co-host materials are selected from the classes of the oligoarylenes, comprising anthracene, benzanthracene and/or pyrene, or atropisomers of these compounds. An oligoarylene in the sense of the present invention is intended to be taken to mean a compound in which at least three aryl or arylene groups are bonded to one another.

Preferred host materials are selected, in particular, from compounds of the formula (H-1), $$Ar^4—(Ar^5)_p—Ar^6 \quad (H\text{-}1)$$

where $Ar^4$, $Ar^5$, $Ar^6$ are on each occurrence, identically or differently, an aryl or heteroaryl group having 5 to 30 aromatic ring atoms, which may optionally be substituted, and p represents an integer in the range from 1 to 5; the sum of the π electrons in $Ar^4$, $Ar^5$ and $Ar^6$ is at least 30 if p=1 and at least 36 if p=2 and at least 42 if p=3.

In the compounds of the formula (H-1), the group $Ar^5$ particularly preferably stands for anthracene, and the groups $Ar^4$ and $Ar^6$ are bonded in the 9- and 10-position, where these groups may optionally be substituted. Very particularly preferably, at least one of the groups $Ar^4$ and/or $Ar^6$ is a condensed aryl group selected from 1- or 2-naphthyl, 2-, 3- or 9-phenanthrenyl or 2-, 3-, 4-, 5-, 6- or 7-benzanthracenyl. Anthracene-based compounds are described in US 2007/0092753 A1 and US 2007/0252517 A1, for example 2-(4-methylphenyl)-9,10-di-(2-naphthyl)anthracene, 9-(2-naphthyl)-10-(1,1'-biphenyl)anthracene and 9,10-bis[4-(2,2-diphenylethenyl)phenyl]anthracene, 9,10-diphenylanthracene, 9,10-bis(phenylethynyl)anthracene and 1,4-bis(9'-ethynylanthracenyl)benzene. Preference is also given to compounds containing two anthracene units (US 2008/0193796 A1), for example 10,10'-bis[1,1',4',1"]terphenyl-2-yl-9,9'-bisanthracenyl.

Further preferred compounds are derivatives of arylamine, styrylamine, fluorescein, diphenylbutadiene, tetraphenylbutadiene, cyclopentadiene, tetraphenylcyclopentadiene, pentaphenylcyclopentadiene, coumarine, oxadiazole, bisbenzoxazoline, oxazole, pyridine, pyrazine, imine, benzothiazole, benzoxazole, benzimidazole (US 2007/0092753 A1), for example 2,2',2"-(1,3,5-phenylene)tris[1-phenyl-1H-benzimidazole], aldazine, stilbene, styrylarylene derivatives, for example 9,10-bis[4-(2,2-diphenylethenyl)phenyl]anthracene, and distyrylarylene derivatives (U.S. Pat. No. 5,121,029), diphenylethylene, vinylanthracene, diaminocarbazole, pyran, thiopyran, diketopyrrolopyrrole, polymethine, cinnamic acid esters and fluorescent dyes.

Particular preference is given to derivatives of arylamine and styrylamine, for example TNB (=4,4'-bis[N-(1-naphthyl)-N-(2-naphthyl)amino]biphenyl). Metal-oxinoid complexes, such as LiQ or AlQ$_3$, can be used as co-hosts.

Preferred compounds with oligoarylene as matrix are disclosed in US 2003/0027016 A1, U.S. Pat. No. 7,326,371 B2, US 2006/043858 A, WO 2007/114358, WO 2008/145239, JP 3148176 B2, EP 1009044, US 2004/018383, WO 2005/061656 A1, EP 0681019B1, WO 2004/013073A1, U.S. Pat. No. 5,077,142, WO 2007/065678 and DE 102009005746, where particularly preferred compounds are described by the formulae H-2 to H-8.

formula H-2 formula H-3 formula H-4 formula H-5

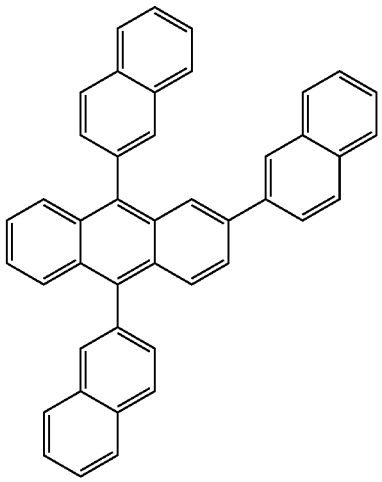

formula H-6

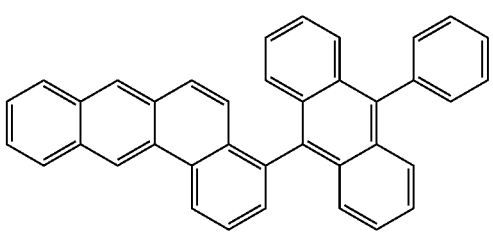

formula H-7

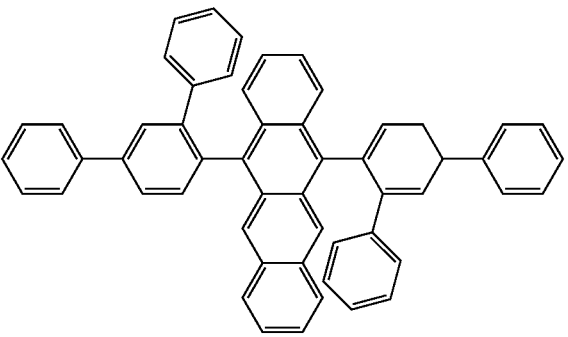

formula H-8

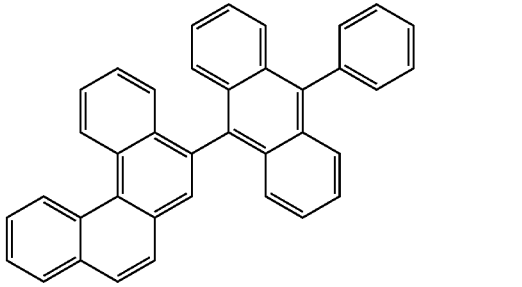

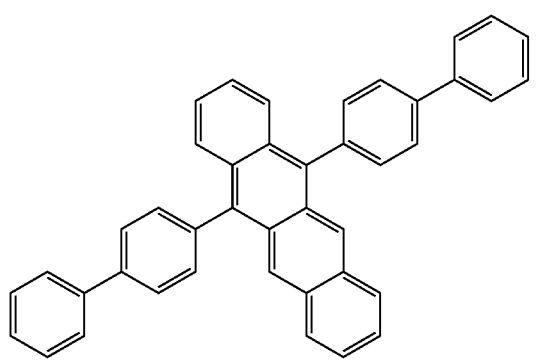

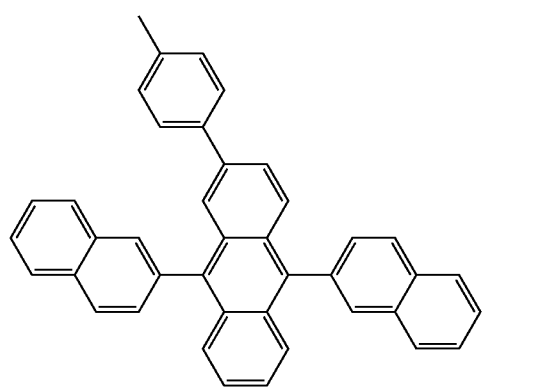

Furthermore, compounds which can be employed as host or matrix include materials which are employed together with phosphorescent emitters.

These compounds, which can also be employed as structural elements in polymers, include CBP (N,N-biscarbazolylbiphenyl), carbazole derivatives (for example in accordance with WO 2005/039246, US 2005/0069729, JP 2004/288381, EP 1205527 or WO 2008/086851), azacarbazoles (for example in accordance with EP 1617710, EP 1617711, EP 1731584 or JP 2005/347160), ketones (for example in accordance with WO 2004/093207 or in accordance with DE 102008033943), phosphine oxides, sulfoxides and sulfones (for example in accordance with WO 2005/003253), oligophenylenes, aromatic amines (for example in accordance with US 2005/0069729), bipolar matrix materials (for example in accordance with WO 2007/137725), silanes (for example in accordance with WO 2005/111172), 9,9-diarylfluorene derivatives (for example in accordance with DE 102008017591), azaboroles or boronic esters (for example in accordance with WO 2006/117052), triazine derivatives (for example in accordance with DE 102008036982), indolocarbazole derivatives (for example in accordance with WO 2007/063754 or WO 2008/056746), indenocarbazole derivatives (for example in accordance with DE 102009023155 and DE 102009031021), diazaphosphole derivatives (for example in accordance with DE 102009022858), triazole derivatives, oxazoles and oxazole derivatives, imidazole derivatives, polyarylalkane derivatives, pyrazoline derivatives, pyrazolone derivatives, distyrylpyrazine derivatives, thiopyran dioxide derivatives, phenylenediamine derivatives, tertiary aromatic amines, styrylamines, amino-substituted chalcone derivatives, indoles, hydrazone derivatives, stilbene derivatives, silazane derivatives, aromatic dimethylidene compounds, carbodiimide derivatives, metal complexes of 8-hydroxyquinoline derivatives, such as, for example, AlQ₃, which may also contain triarylaminophenol ligands (US 2007/0134514 A1), metal complex/polysilane compounds, and thiophene, benzothiophene and dibenzothiophene derivatives.

Examples of preferred carbazole derivatives are mCP (=1,3-N,N-dicarbazolylbenzene (=9,9'-(1,3-phenylene)bis-9H-carbazole)) (formula H-9), CDBP (=9,9'-(2,2'-dimethyl[1,1'-biphenyl]-4,4'-diyl)bis-9H-carbazole), 1,3-bis(N,N'-dicarbazolyl)benzene (=1,3-bis(carbazol-9-yl)benzene), PVK (polyvinylcarbazole), 3,5-di(9H-carbazol-9-yl)biphenyl and CMTTP (formula H-10). Particularly referred compounds are disclosed in US 2007/0128467 A1 and US 2005/0249976 A1 (formulae H-11 and H-13).

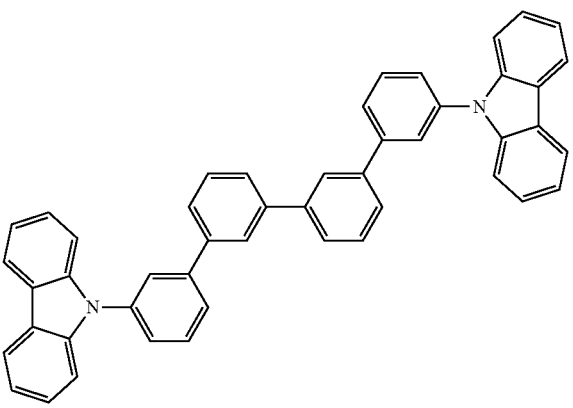

CMTTP

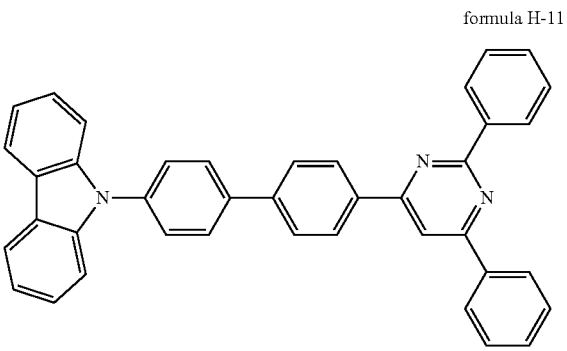

formula H-11

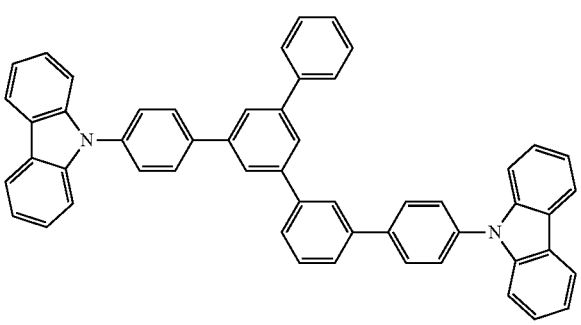

formula H-12

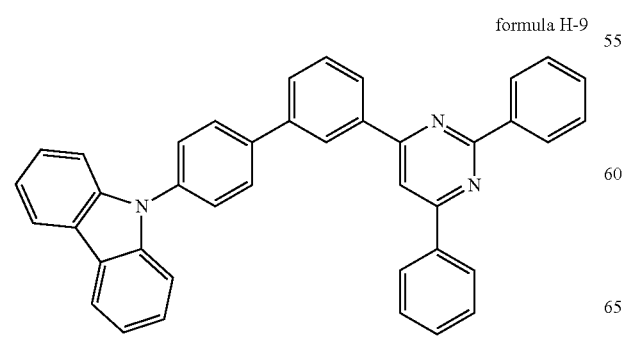

formula H-9

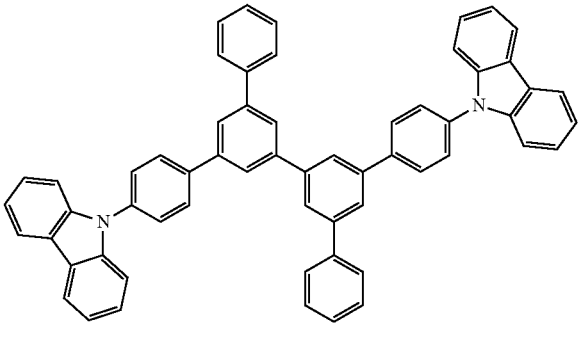

formula H-13

Preferred tetraaryl-Si compounds are disclosed, for example, in US 2004/0209115, US 2004/0209116, US 2007/0087219 A1 and in H. Gilman, E. A. Zuech, Chemistry & Industry (London, United Kingdom), 1960, 120.

Particularly preferred tetraaryl-Si compounds are described by the formulae H-14 to H-20.

formula H-14

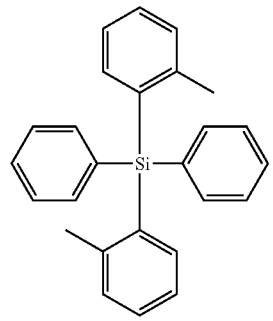

UGH1 formula H-15

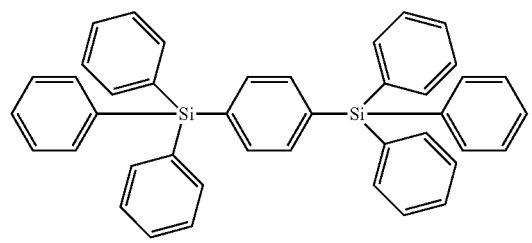

UGH2 formula H-16

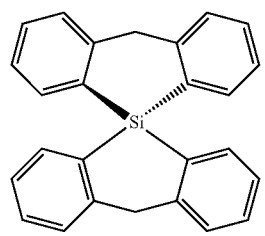

UGH4 formula H-17

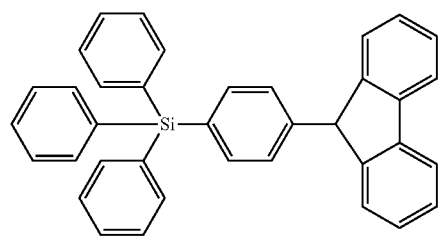

TPSi—F
Triphenyl-[4-(9-phenyl-9H-fluoren-9-yl)phenyl]silane formula H-18

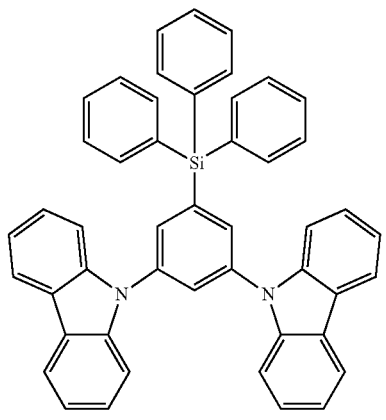

SimCP formula H-19

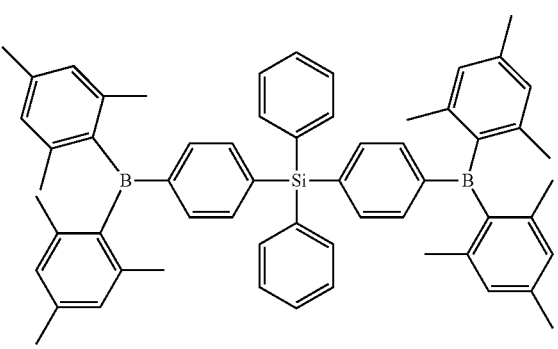

formula H-20

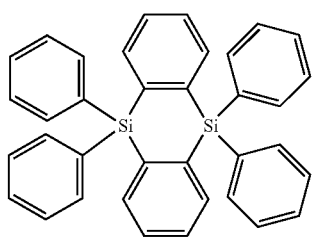

formula H-21

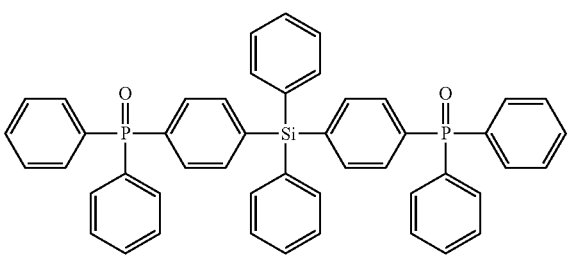

Particularly preferred compounds from group 4 for the preparation of the matrix for phosphorescent dopants are disclosed, inter alia, in DE 102009022858, DE 102009023155, EP 652273 B1, WO 2007/063754 and WO 2008/056746, where particularly preferred compounds are described by the formulae H-21 to H-24.

formula H-22

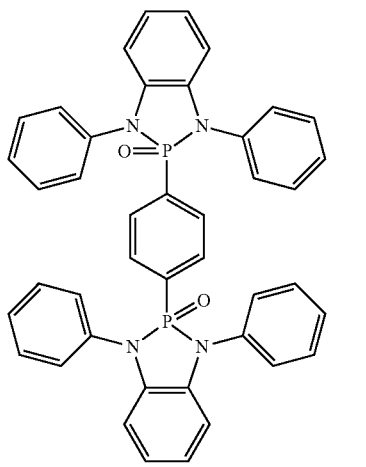

formula H-23

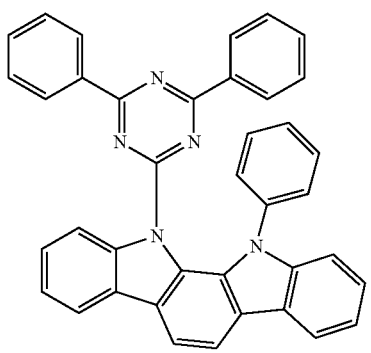

formula H-24

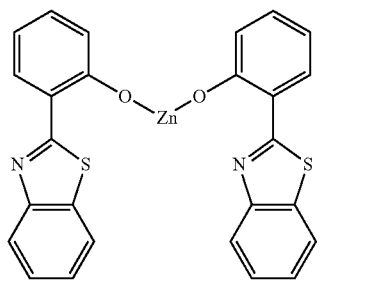

formula H-25

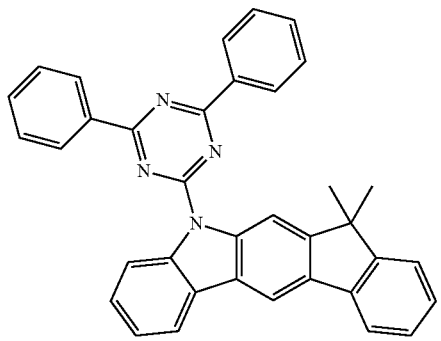

With respect to the functional compounds which can be employed in accordance with the invention and which can serve as host material, especial preference is given to substances which contain at least one nitrogen atom. These preferably include aromatic amines, triazine derivatives and carbazole derivatives. Thus, carbazole derivatives in particular exhibit surprisingly high efficiency. Triazine derivatives result in unexpectedly long lifetimes of the electronic devices.

It may also be preferred to employ a plurality of different matrix materials as a mixture, in particular at least one electron-conducting matrix material and at least one hole-conducting matrix material. Preference is likewise given to the use of a mixture of a charge-transporting matrix material and an electrically inert matrix material which is not in involved in the charge transport to a significant extent, if at all, as described, for example, in WO 2010/108579.

It is furthermore possible to employ compounds which improve the transition from the singlet state to the triplet state and which, employed in support of the functional compounds having emitter properties, improve the phosphorescence properties of these compounds. Suitable for this purpose are, in particular, carbazole and bridged carbazole dimer units, as described, for example, in WO 2004/070772 A2 and WO 2004/113468 A1. Also suitable for this purpose are ketones, phosphine oxides, sulfoxides, sulfones, silane derivatives and similar compounds, as described, for example, in WO 2005/040302 A1.

Furthermore, the formulations may comprise a wide-band-gap material as functional material. Wide-band-gap material is taken to mean a material in the sense of the disclosure content of U.S. Pat. No. 7,294,849. These systems exhibit particularly advantageous performance data in electroluminescent devices.

The compound employed as wide-band-gap material can preferably have a band gap of 2.5 eV or more, preferably 3.0 eV or more, particularly preferably 3.5 eV or more. The band gap can be calculated, inter alia, by means of the energy levels of the highest occupied molecular orbital (HOMO) and the lowest unoccupied molecular orbital (LUMO).

Furthermore, the formulations may comprise a hole-blocking material (HBM) as functional material. A hole-blocking material denotes a material which prevents or minimises the transmission of holes (positive charges) in a multilayer system, in particular if this material is arranged in the form of a layer adjacent to an emission layer or a hole-conducting layer. In general, a hole-blocking material has a lower HOMO level than the hole-transport material in the adjacent layer. Hole-blocking layers are frequently arranged between the light-emitting layer and the electron-transport layer in OLEDs.

It is basically possible to employ any known hole-blocking material. In addition to other hole-blocking materials described elsewhere in the present application, advantageous hole-blocking materials are metal complexes (US 2003/0068528), such as, for example, bis(2-methyl-8-quinolinolato)(4-phenylphenolato)aluminium(III) (BAlQ). Fac-tris(1-phenylpyrazolato-N,C2)iridium(III) (Ir(ppz)$_3$) is likewise employed for this purpose (US 2003/0175553 A1). Phenanthroline derivatives, such as, for example, BCP, or phthalimides, such as, for example, TMPP, can likewise be employed.

Furthermore, advantageous hole-blocking materials are described in WO 00/70655 A2, WO 01/41512 and WO 01/93642 A1.

Furthermore, the formulations may comprise an electron-blocking material (EBM) as functional material. An electron-blocking material denotes a material which prevents or minimises the transmission of electrons in a multilayer system, in particular if this material is arranged in the form of a layer adjacent to an emission layer or an electron-conducting layer. In general, an electron-blocking material has a higher LUMO level than the electron-transport material in the adjacent layer.

It is basically possible to employ any known electron-blocking material. In addition to other electron-blocking materials described elsewhere in the present application, advantageous electron-blocking materials are transition-metal complexes, such as, for example, Ir(ppz)$_3$ (US 2003/0175553).

The electron-blocking material can preferably be selected from amines, triarylamines and derivatives thereof.

Furthermore, the functional compounds which can be employed as organic functional materials in the formulations preferably have, if they are low-molecular-weight compounds, a molecular weight of ≤3,000 g/mol, particularly preferably ≤2,000 g/mol and especially preferably ≤1,800 g/mol.

Of particular interest are furthermore functional compounds which are distinguished by a high glass-transition temperature. In this connection, particularly preferred functional compounds which can be employed as organic functional material in the formulations are those which have a glass-transition temperature of ≥70° C., preferably ≥100° C., particularly preferably ≥125° C. and especially preferably ≥150° C., determined in accordance with DIN 51005.

The formulations may also comprise polymers as organic functional materials. The compounds described above as organic functional materials, which frequently have a relatively low molecular weight, can also be mixed with a polymer. It is likewise possible to incorporate these compounds covalently into a polymer. This is possible, in particular, with compounds which are substituted by reactive leaving groups, such as bromine, iodine, chlorine, boronic acid or boronic acid ester, or by reactive, polymerisable groups, such as olefins or oxetanes. These can be used as monomers for the production of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as crosslinked or uncrosslinked layer.

Polymers which can be employed as organic functional materials frequently contain units or structural elements which have been described in the context of the compounds described above, inter alia those as disclosed and extensively listed in WO 02/077060 A1, in WO 2005/014689 A2 and in WO 2011/076314 A1. These are incorporated into the present application by way of reference. The functional materials can originate, for example, from the following classes:

Group 1: structural elements which are able to generate hole-injection and/or hole-transport properties;
Group 2: structural elements which are able to generate electron-injection and/or electron-transport properties;
Group 3: structural elements which combine the properties described in relation to groups 1 and 2;
Group 4: structural elements which have light-emitting properties, in particular phosphorescent groups;
Group 5: structural elements which improve the transition from the so-called singlet state to the triplet state;
Group 6: structural elements which influence the morphology or also the emission colour of the resultant polymers;
Group 7: structural elements which are typically used as backbone.

The structural elements here may also have various functions, so that a clear assignment need not be advantageous. For example, a structural element of group 1 may likewise serve as backbone.

The polymer having hole-transport or hole-injection properties employed as organic functional material, containing structural elements from group 1, may preferably contain units which correspond to the hole-transport or hole-injection materials described above.

Further preferred structural elements of group 1 are, for example, triarylamine, benzidine, tetraaryl-para-phenylenediamine, carbazole, azulene, thiophene, pyrrole and furan derivatives and further O-, S- or N-containing heterocycles having a high HOMO. These arylamines and heterocycles preferably have an HOMO of above −5.8 eV (against vacuum level), particularly preferably above −5.5 eV.

Preference is given, inter alia, to polymers having hole-transport or hole-injection properties, containing at least one of the following recurring units of the formula HTP-1:

HTP-1 in which the symbols have the following meaning:

Ar$^1$ is, in each case identically or differently for different recurring units, a single bond or a monocyclic or polycyclic aryl group, which may optionally be substituted;

Ar$^2$ is, in each case identically or differently for different recurring units, a monocyclic or polycyclic aryl group, which may optionally be substituted;

Ar$^3$ is, in each case identically or differently for different recurring units, a monocyclic or polycyclic aryl group, which may optionally be substituted;

m is 1, 2 or 3.

Particular preference is given to recurring units of the formula HTP-1 which are selected from the group consisting of units of the formulae HTP-1A to HTP-1C:

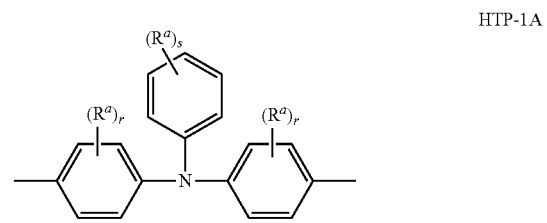

HTP-1A

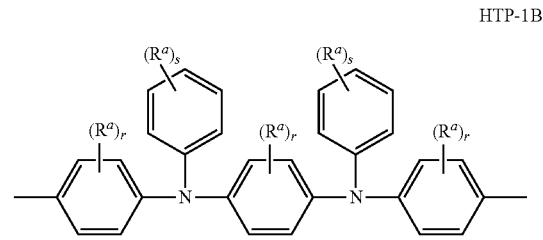

HTP-1B

-continued

HTP-1C

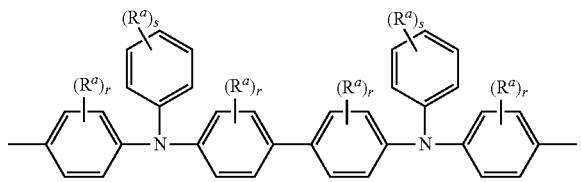

in which the symbols have the following meaning:
$R^a$ is on each occurrence, identically or differently, H, a substituted or unsubstituted aromatic or heteroaromatic group, an alkyl, cycloalkyl, alkoxy, aralkyl, aryloxy, arylthio, alkoxycarbonyl, silyl or carboxyl group, a halogen atom, a cyano group, a nitro group or a hydroxyl group;
r is 0, 1, 2, 3 or 4, and
s is 0, 1, 2, 3, 4 or 5.

Preference is given, inter alia, to polymers having hole-transport or hole-injection properties, containing at least one of the following recurring units of the formula HTP-2:

HTP-2 in which the symbols have the following meaning:
$T^1$ and $T^2$ are selected independently from thiophene, selenophene, thieno[2,3-b]thiophene, thieno[3,2-b]thiophene, dithienothiophene, pyrrole and aniline, where these groups may be substituted by one or more radicals $R^b$;
$R^b$ is selected independently on each occurrence from halogen, —CN, —NC, —NCO, —NCS, —OCN, —SCN, —C(=O)NR$^0$R$^{00}$, —C(=O)X, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, an optionally substituted silyl, carbyl or hydrocarbyl group having 1 to 40 carbon atoms, which may optionally be substituted and may optionally contain one or more heteroatoms;
$R^0$ and $R^{00}$ are each independently H or an optionally substituted carbyl or hydrocarbyl group having 1 to 40 carbon atoms, which may optionally be substituted and may optionally contain one or more heteroatoms;
$Ar^7$ and $Ar^8$ represent, independently of one another, a monocyclic or polycyclic aryl or heteroaryl group, which may optionally be substituted and may optionally be bonded to the 2,3-position of one or both adjacent thiophene or selenophene groups;
c and e are, independently of one another, 0, 1, 2, 3 or 4, where $1<c+e\le 6$;
d and f are, independently of one another, 0, 1, 2, 3 or 4.

Preferred examples of polymers having hole-transport or hole-injection properties are described, inter alia, in WO 2007/131582 A1 and WO 2008/009343A1.

The polymer having electron-injection and/or electron-transport properties employed as organic functional material, containing structural elements from group 2, may preferably contain units which correspond to the electron-injection and/or electron-transport materials described above.

Further preferred structural elements of group 2 which have electron-injection and/or electron-transport properties are derived, for example, from pyridine, pyrimidine, pyridazine, pyrazine, oxadiazole, quinoline, quinoxaline and phenazine groups, but also triarylborane groups or further O-, S- or N-containing heterocycles having a low LUMO level. These structural elements of group 2 preferably have an LUMO of below −2.7 eV (against vacuum level), particularly preferably below −2.8 eV.

The organic functional material can preferably be a polymer which contains structural elements from group 3, where structural elements which improve the hole and electron mobility (i.e. structural elements from groups 1 and 2) are connected directly to one another. Some of these structural elements can serve as emitters here, where the emission colours may be shifted, for example, into the green, red or yellow. Their use is therefore advantageous, for example, for the generation of other emission colours or a broad-band emission by polymers which originally emit in blue.

The polymer having light-emitting properties employed as organic functional material, containing structural elements from group 4, may preferably contain units which correspond to the emitter materials described above. Preference is given here to polymers containing phosphorescent groups, in particular the emitting metal complexes described above which contain corresponding units containing elements from groups 8 to 10 (Ru, Os, Rh, Ir, Pd, Pt).

The polymer employed as organic functional material containing units of group 5 which improve the transition from the so-called singlet state to the triplet state can preferably be employed in support of phosphorescent compounds, preferably the polymers containing structural elements of group 4 described above. A polymeric triplet matrix can be used here.

Suitable for this purpose are, in particular, carbazole and connected carbazole dimer units, as described, for example, in DE 10304819 A1 and DE 10328627 A1. Also suitable for this purpose are ketone, phosphine oxide, sulfoxide, sulfone and silane derivatives and similar compounds, as described, for example, in DE 10349033 A1. Furthermore, preferred structural units can be derived from compounds which have been described above in connection with the matrix materials employed together with phosphorescent compounds.

The further organic functional material is preferably a polymer containing units of group 6 which influence the morphology and/or the emission colour of the polymers. Besides the polymers mentioned above, these are those which have at least one further aromatic or another conjugated structure which do not count amongst the above-mentioned groups. These groups accordingly have only little or no effect on the charge-carrier mobilities, the non-organometallic complexes or the singlet-triplet transition.

The polymers may also include cross-linkable groups such as styrene, benzocyclobutene, epoxide and oxetane moieties.

Structural units of this type are able to influence the morphology and/or the emission colour of the resultant polymers. Depending on the structural unit, these polymers can therefore also be used as emitters.

In the case of fluorescent OLEDs, preference is therefore given to aromatic structural elements having 6 to 40 C atoms or also tolan, stilbene or bisstyrylarylene derivative units, each of which may be substituted by one or more radicals. Particular preference is given here to the use of groups derived from 1,4-phenylene, 1,4-naphthylene, 1,4- or 9,10-anthrylene, 1,6-, 2,7- or 4,9-pyrenylene, 3,9- or 3,10-perylenylene, 4,4'-biphenylene, 4,4''-terphenylylene, 4,4'-bi-1,1'-naphthylylene, 4,4'-tolanylene, 4,4'-stilbenylene or 4,4''-bisstyrylarylene derivatives.

The polymer employed as organic functional material preferably contains units of group 7, which preferably contain aromatic structures having 6 to 40 C atoms which are frequently used as backbone.

These include, inter alia, 4,5-dihydropyrene derivatives, 4,5,9,10-tetrahydropyrene derivatives, fluorene derivatives, which are disclosed, for example, in U.S. Pat. No. 5,962, 631, WO 2006/052457 A2 and WO 2006/118345A1, 9,9-spirobifluorene derivatives, which are disclosed, for example, in WO 2003/020790 A1, 9,10-phenanthrene derivatives, which are disclosed, for example, in WO 2005/104264 A1, 9,10-dihydrophenanthrene derivatives, which are disclosed, for example, in WO 2005/014689 A2, 5,7-dihydrodibenzoxepine derivatives and cis- and trans-indenofluorene derivatives, which are disclosed, for example, in WO 2004/041901 A1 and WO 2004/113412 A2, and binaphthylene derivatives, which are disclosed, for example, in WO 2006/063852 A1, and further units which are disclosed, for example, in WO 2005/056633A1, EP 1344788A1, WO 2007/043495A1, WO 2005/033174 A1, WO 2003/099901 A1 and DE 102006003710.

Particular preference is given to structural units of group 7 which are selected from fluorene derivatives, which are disclosed, for example, in U.S. Pat. No. 5,962,631, WO 2006/052457 A2 and WO 2006/118345 A1, spirobifluorene derivatives, which are disclosed, for example, in WO 2003/020790 A1, benzofluorene, dibenzofluorene, benzothiophene and dibenzofluorene groups and derivatives thereof, which are disclosed, for example, in WO 2005/056633 A1, EP 1344788 A1 and WO 2007/043495 A1.

Especially preferred structural elements of group 7 are represented by the general formula PB-1:

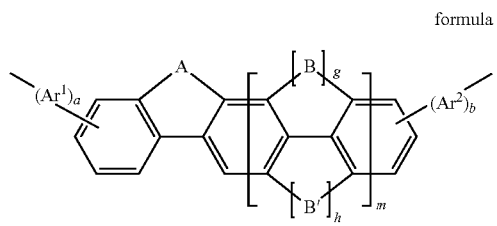

formula PB-1 in which the symbols and indices have the following meanings:

A, B and B' are each, also for different recurring units, identically or differently, a divalent group, which is preferably selected from —CR$^c$R$^d$—, —NR$^c$—, —PR$^c$—, —O—, —S—, —SO—, —SO$_2$—, —CO—, —CS—, —CSe—, —P(=O)R$^c$—, —P(=S)R$^c$— and —SiR$^c$R$^d$—;

R$^c$ and R$^d$ are selected on each occurrence, independently, from H, halogen, —CN, —NC, —NCO, —NCS, —OCN, —SCN, —C(=O)NR$^0$R$^{00}$, —C(=O)X, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, an optionally substituted silyl, carbyl or hydrocarbyl group having 1 to 40 carbon atoms, which may optionally be substituted and may optionally contain one or more heteroatoms, where the groups R$^c$ and R$^d$ may optionally form a spiro group with a fluorene radical to which they are bonded;

X is halogen;

R$^0$ and R$^{00}$ are each, independently, H or an optionally substituted carbyl or hydrocarbyl group having 1 to 40 carbon atoms, which may optionally be substituted and may optionally contain one or more heteroatoms;

g is in each case, independently, 0 or 1 and h is in each case, independently, 0 or 1, where the sum of g and h in a sub-unit is preferably 1;

m is an integer ≥1;

Ar$^1$ and Ar$^2$ represent, independently of one another, a monocyclic or polycyclic aryl or heteroaryl group, which may optionally be substituted and may optionally be bonded to the 7,8-position or the 8,9-position of an indenofluorene group;

a and b are, independently of one another, 0 or 1.

If the groups R$^c$ and R$^d$ form a spiro group with the fluorene group to which these groups are bonded, this group preferably represents a spirobifluorene.

Particular preference is given to recurring units of the formula PB-1 which are selected from the group consisting of units of the formulae PB-1A to PB-1E:

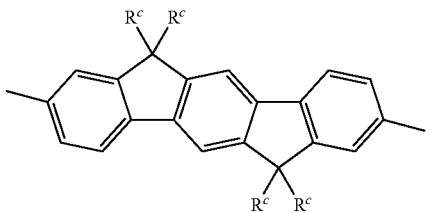

formula PB-1A

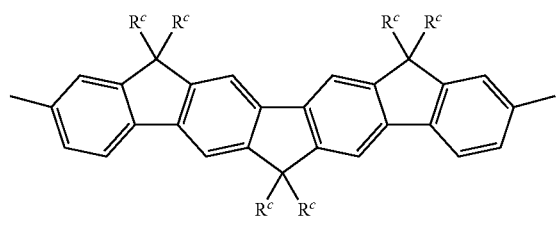

formula PB-1B

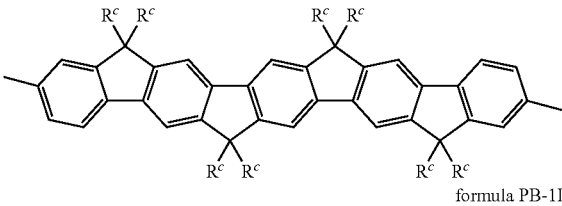

formula PB-1C

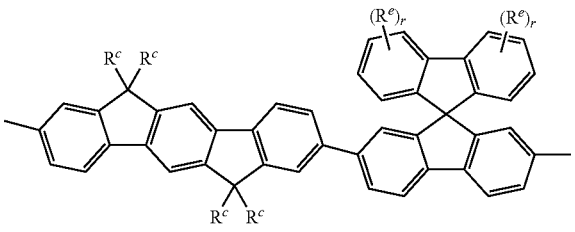

formula PB-1D

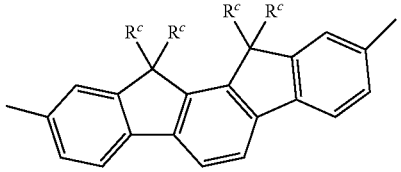

formula PB-1E where R$^c$ has the meaning described above for formula PB-1, r is 0, 1, 2, 3 or 4, and R$^e$ has the same meaning as the radical R$^c$.

R$^e$ is preferably —F, —Cl, —Br, —I, —CN, —NO$_2$, —NCO, —NCS, —OCN, —SCN, —C(=O)NR$^0$R$^{00}$, —C(=O)X, —C(=O)R$^0$, —NR$^0$R$^{00}$, an optionally substituted silyl, aryl or heteroaryl group having 4 to 40, preferably 6 to 20, C atoms, or a straight-chain, branched or cyclic alkyl, alkoxy, alkylcarbonyl, alkoxycarbonyl, alkylcarbonyloxy or alkoxycarbonyloxy group having 1 to 20, preferably 1 to 12, C atoms, where one or more hydrogen atoms may optionally be substituted by F or Cl, and the groups $R^o$, $R^{oo}$ and X have the meaning described above for formula PB-1.

Particular preference is given to recurring units of the formula PB-1 which are selected from the group consisting of units of the formulae PB-1F to PB-1I:

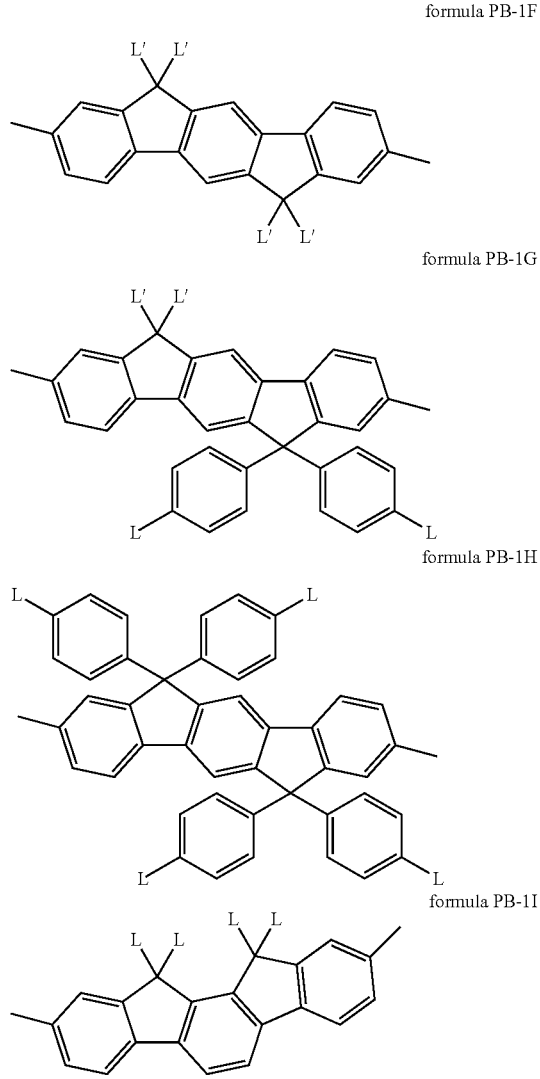

in which the symbols have the following meaning:
L is H, halogen or an optionally fluorinated, linear or branched alkyl or alkoxy group having 1 to 12 C atoms and preferably stands for H, F, methyl, i-propyl, t-butyl, n-pentoxy or trifluoromethyl; and
L' is an optionally fluorinated, linear or branched alkyl or alkoxy group having 1 to 12 C atoms and preferably stands for n-octyl or n-octyloxy.

For carrying out the present invention, preference is given to polymers which contain more than one of the structural elements of groups 1 to 7 described above. It may furthermore be provided that the polymers preferably contain more than one of the structural elements from one group described above, i.e. comprise mixtures of structural elements selected from one group.

Particular preference is given, in particular, to polymers which, besides at least one structural element which has light-emitting properties (group 4), preferably at least one phosphorescent group, additionally contain at least one further structural element of groups 1 to 3, 5 or 6 described above, where these are preferably selected from groups 1 to 3.

The proportion of the various classes of groups, if present in the polymer, can be in broad ranges, where these are known to the person skilled in the art. Surprising advantages can be achieved if the proportion of one class present in a polymer, which is in each case selected from the structural elements of groups 1 to 7 described above, is preferably in each case ≥5 mol %, particularly preferably in each case ≥10 mol %.

The preparation of white-emitting copolymers is described in detail, inter alia, in DE 10343606 A1.

In order to improve the solubility, the polymers may contain corresponding groups. It may preferably be provided that the polymers contain substituents, so that on average at least 2 non-aromatic carbon atoms, particularly preferably at least 4 and especially preferably at least 8 non-aromatic carbon atoms are present per recurring unit, where the average relates to the number average. Individual carbon atoms here may be replaced, for example, by O or S. However, it is possible for a certain proportion, optionally all recurring units, to contain no substituents which contain non-aromatic carbon atoms. Short-chain substituents are preferred here, since long-chain substituents can have adverse effects on layers which can be obtained using organic functional materials. The substituents preferably contain at most 12 carbon atoms, preferably at most 8 carbon atoms and particularly preferably at most 6 carbon atoms in a linear chain.

The polymer employed in accordance with the invention as organic functional material can be a random, alternating or regioregular copolymer, a block copolymer or a combination of these copolymer forms.

In a further embodiment, the polymer employed as organic functional material can be a non-conjugated polymer having side chains, where this embodiment is particularly important for phosphorescent OLEDs based on polymers. In general, phosphorescent polymers can be obtained by free-radical copolymerisation of vinyl compounds, where these vinyl compounds contain at least one unit having a phosphorescent emitter and/or at least one charge-transport unit, as is disclosed, inter alia, in U.S. Pat. No. 7,250,226 B2. Further phosphorescent polymers are described, inter alia, in JP 2007/211243 A2, JP 2007/197574 A2, U.S. Pat. No. 7,250,226 B2 and JP 2007/059939 A.

In a further preferred embodiment, the non-conjugated polymers contain backbone units, which are connected to one another by spacer units. Examples of such triplet emitters which are based on non-conjugated polymers based on backbone units are disclosed, for example, in DE 102009023154.

In a further preferred embodiment, the non-conjugated polymer can be designed as fluorescent emitter. Preferred fluorescent emitters which are based on non-conjugated polymers having side chains contain anthracene or benzanthracene groups or derivatives of these groups in the side chain, where these polymers are disclosed, for example, in JP 2005/108556, JP 2005/285661 and JP 2003/338375.

These polymers can frequently be employed as electron- or hole-transport materials, where these polymers are preferably designed as non-conjugated polymers.

Furthermore, the functional compounds employed as organic functional materials in the formulations preferably have, in the case of polymeric compounds, a molecular weight $M_w$ of ≥10,000 g/mol, particularly preferably ≥20,000 g/mol and especially preferably ≥50,000 g/mol.

The molecular weight $M_w$ of the polymers here is preferably in the range from 10,000 to 2,000,000 g/mol, particularly preferably in the range from 20,000 to 1,000,000 g/mol and very particularly preferably in the range from 50,000 to 300,000 g/mol. The molecular weight $M_w$ is determined by means of GPC (=gel permeation chromatography) against an internal polystyrene standard.

The publications cited above for description of the functional compounds are incorporated into the present application by way of reference for disclosure purposes.

The formulations according to the invention may comprise all organic functional materials which are necessary for the production of the respective functional layer of the electronic device. If, for example, a hole-transport, hole-injection, electron-transport or electron-injection layer is built up precisely from one functional compound, the formulation comprises precisely this compound as organic functional material. If an emission layer comprises, for example, an emitter in combination with a matrix or host material, the formulation comprises, as organic functional material, precisely the mixture of emitter and matrix or host material, as described in greater detail elsewhere in the present application.

Besides the said components, the formulation according to the invention may comprise further additives and processing assistants. These include, inter alia, surface-active substances (surfactants), lubricants and greases, additives which modify the viscosity, additives which increase the conductivity, dispersants, hydrophobicising agents, adhesion promoters, flow improvers, antifoams, deaerating agents, diluents, which may be reactive or unreactive, fillers, assistants, processing assistants, dyes, pigments, stabilisers, sensitisers, nanoparticles and inhibitors.

The present invention furthermore relates to a process for the preparation of a formulation according to the invention, wherein the ester solvent, the optional further solvent and the organic functional material, which can be employed for the production of functional layers of electronic devices, are mixed, are mixed.

A formulation in accordance with the present invention can be employed for the production of a layer or multilayered structure in which the organic functional materials are present in layers, as are required for the production of preferred electronic or opto-electronic components, such as OLEDs.

The formulation of the present invention can preferably be employed for the formation of functional layers on a substrate or one of the layers applied to the substrate.

The present invention likewise relates to a process for the production of an electronic device in which at least one layer of the electronic device is prepared in that a formulation according to the invention is applied to a substrate and subsequently dried.

The formulations to prepare the functional layers can be applied, for example, by slot-die coating, curtain coating, flood coating, dip coating, spray coating, spin coating, screen printing, relief printing, gravure printing, rotary printing, roller coating, flexographic printing, offset printing or nozzle printing, preferably inkjet printing on a substrate or one of the layers applied to the substrate.

After the application of a formulation according to the invention to a substrate or a functional layer already applied, a drying step can be carried out in order to remove the solvent from the continuous phase described above. The drying can preferably be carried out at relatively low temperature such as room temperature and over a relatively long period in order to avoid bubble formation and to obtain a uniform coating. Preferably, the drying is carried out at a pressure in the range from $10^{-6}$ mbar to 1 bar, particularly preferably in the range from $10^{-6}$ mbar to 100 mbar and especially preferably in the range from $10^{-6}$ mbar to 10 mbar. The duration of the drying depends on the degree of drying to be achieved, where small amounts of residual solvents and or other volatile components like e.g. water can optionally be removed at relatively high temperature and in combination with sintering, which is preferably to be carried out.

The drying step is followed by an annealing step which preferably is carried out at an elevated temperature in the range from 80 to 300° C., particularly preferably from 150 to 250° C. and especially preferably from 160 to 220° C. The drying and the annealing step can be combined and performed as a single step.

It may furthermore be provided that the process is repeated a number of times, with formation of different or identical functional layers. Crosslinking of the functional layer formed can take place here in order to prevent dissolution thereof, as is disclosed, for example, in EP 0 637 899 A1.

The present invention also relates to an electronic device obtainable by a process for the production of an electronic device.

The present invention furthermore relates to an electronic device having at least one functional layer comprising at least one organic functional material which is obtainable by the above-mentioned process for the production of an electronic device.

An electronic device is taken to mean a device comprising two electrodes and at least one functional layer in between, where this functional layer comprises at least one organic or organometallic compound.

The organic electronic device is preferably an organic electroluminescent device (OLED), a polymeric electroluminescent device (PLED), an organic integrated circuit (O-IC), an organic field-effect transistor (O-FET), an organic thin-film transistor (O-TFT), an organic, light-emitting transistor (O-LET), an organic solar cell (O-SC), an organic, optical detector, an organic photoreceptor, an organic field-quench device (O-FQD), an organic electrical sensor, a light-emitting electrochemical cell (LEC) or an organic laser diode (O-laser).

Active components are generally the organic or inorganic materials which are introduced between the anode and the cathode, where these active components effect, maintain and/or improve the properties of the electronic device, for example its performance and/or its lifetime, for example charge-injection, charge-transport or charge-blocking materials, but in particular emission materials and matrix materials. The organic functional material which can be employed for the production of functional layers of electronic devices accordingly preferably comprises an active component of the electronic device.

Organic electroluminescent devices (OLEDs) are a preferred embodiment of the present invention. The OLED comprises a cathode, an anode and at least one emitting layer.

It is furthermore preferred to employ a mixture of two or more triplet emitters together with a matrix. The triplet emitter having the shorter-wave emission spectrum serves as co-matrix here for the triplet emitter having the longer-wave emission spectrum.

The proportion of the matrix material in the emitting layer in this case is preferably between 50 and 99.9% by volume, particularly preferably between 80 and 99.5% by volume and especially preferably between 92 and 99.5% by volume for fluorescent emitting layers and between 70 and 97% by volume for phosphorescent emitting layers.

Correspondingly, the proportion of the dopant is preferably between 0.1 and 50% by volume, particularly preferably between 0.5 and 20% by volume and especially preferably between 0.5 and 8% by volume for fluorescent emitting layers and between 3 and 15% by volume for phosphorescent emitting layers.

An emitting layer of an organic electroluminescent device may also encompass systems which comprise a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

The mixed-matrix systems preferably comprise two or three different matrix materials, particularly preferably two different matrix materials. One of the two materials here is preferably a material having hole-transporting properties or a wide-band-gap material and the other material is a material having electron-transporting properties. However, the desired electron-transporting and hole-transporting properties of the mixed-matrix components may also be combined principally or completely in a single mixed-matrix component, where the further mixed-matrix component(s) fulfil(s) other functions. The two different matrix materials may be present here in a ratio of 1:50 to 1:1, preferably 1:20 to 1:1, particularly preferably 1:10 to 1:1 and especially preferably 1:4 to 1:1. Mixed-matrix systems are preferably employed in phosphorescent organic electroluminescent devices. Further details on mixed-matrix systems can be found, for example, in WO 2010/108579.

Apart from these layers, an organic electroluminescent device may also comprise further layers, for example in each case one or more hole-injection layers, hole-transport layers, hole-blocking layers, electron-transport layers, electron-injection layers, exciton-blocking layers, electron-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. It is possible here for one or more hole-transport layers to be p-doped, for example with metal oxides, such as $MoO_3$ or $WO_3$, or with (per) fluorinated electron-deficient aromatic compounds, and/or for one or more electron-transport layers to be n-doped. It is likewise possible for interlayers, which have, for example, an exciton-blocking function and/or control the charge balance in the electroluminescent device, to be introduced between two emitting layers. However, it should be pointed out that each of these layers does not necessarily have to be present.

The thickness of the layers, for example the hole-transport and/or hole-injection layer, can preferably be in the range from 1 to 500 nm, particularly preferably in the range from 2 to 200 nm.

In a further embodiment of the present invention, the device comprises a plurality of layers. The formulation according to the invention can preferably be employed here for the production of a hole-transport, hole-injection, electron-transport, electron-injection and/or emission layer.

The present invention accordingly also relates to an electronic device which comprises at least three layers, but in a preferred embodiment all said layers, from hole-injection, hole-transport, emission, electron-transport, electron-injection, charge-blocking and/or charge-generation layer and in which at least one layer has been obtained by means of a formulation to be employed in accordance with the invention.

The device may furthermore comprise layers built up from further low-molecular-weight compounds or polymers which have not been applied by the use of formulations according to the invention. These can also be produced by evaporation of low-molecular-weight compounds in a high vacuum.

It may additionally be preferred to use the compounds to be employed not as the pure substance, but instead as a mixture (blend) together with further polymeric, oligomeric, dendritic or low-molecular-weight substances of any desired type. These may, for example, improve the electronic or emission properties of the layer.

In a preferred embodiment of the present invention, the organic electroluminescent device here may comprise one or more emitting layers. If a plurality of emission layers are present, these preferably have a plurality of emission maxima between 380 nm and 750 nm, resulting overall in white emission, i.e. various emitting compounds which are able to fluoresce or phosphoresce are used in the emitting layers. Very particular preference is given to three-layer systems, where the three layers exhibit blue, green and orange or red emission (for the basic structure see, for example, WO 2005/011013). White-emitting devices are suitable, for example, as backlighting of LCD displays or for general lighting applications.

It is also possible for a plurality of OLEDs to be arranged one above the other, enabling a further increase in efficiency with respect to the light yield to be achieved.

In order to improve the out-coupling of light, the final organic layer on the light-exit side in OLEDs can, for example, also be in the form of a nano-foam, resulting in a reduction in the proportion of total reflection.

Preference is furthermore given to an OLED in which one or more layers are applied by means of a sublimation process, in which the materials are applied by vapour deposition in vacuum sublimation units at a pressure below $10^{-5}$ mbar, preferably below $10^{-6}$ mbar, particularly preferably below $10^{-7}$ mbar.

It may furthermore be provided that one or more layers of an electronic device according to the invention are applied by means of the OVPD (organic vapour phase deposition) process or with the aid of carrier-gas sublimation, in which the materials are applied at a pressure between $10^{-5}$ mbar and 1 bar.

It may furthermore be provided that one or more layers of an electronic device according to the invention are produced from solution, such as, for example, by spin coating, or by means of any desired printing process, such as, for example, screen printing, flexographic printing or offset printing, but particularly preferably LITI (light induced thermal imaging, thermal transfer printing) or inkjet printing.

These layers may also be applied by a process in which no compound of the formula (I) or (II) is employed. An orthogonal solvent can preferably be used here, which, although dissolving the functional material of a layer to be applied, does not dissolve the layer to which the functional material is applied.

The device usually comprises a cathode and an anode (electrodes). The electrodes (cathode, anode) are selected for the purposes of the present invention in such a way that their band energies correspond as closely as possible to those of the adjacent, organic layers in order to ensure highly efficient electron or hole injection.

The cathode preferably comprises metal complexes, metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali-metal or alkaline-earth metal fluorides, but also the corresponding oxides (for example LiF, $Li_2O$, $BaF_2$, MgO, NaF, etc.). The layer thickness of this layer is preferably between 0.1 and 10 nm, particularly preferably between 0.2 and 8 nm, especially preferably between 0.5 and 5 nm.

The anode preferably comprises materials having a high work function. The anode preferably has a potential greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent in order to facilitate either irradiation of the organic material (O-SCs) or the coupling-out of light (OLEDs/PLEDs, O-lasers). A preferred structure uses a transparent anode. Preferred anode materials here are conductive, mixed metal oxides. Particular preference is given to indium tin oxide (ITO) or indium zinc oxide (IZO). Preference is furthermore given to conductive, doped organic materials, in particular conductive, doped polymers, such as, for example, poly(ethylenedioxythiophene) (PEDOT) and polyaniline (PANI) or derivatives of these polymers. It is furthermore preferred for a p-doped hole-transport material to be applied as hole-injection layer to the anode, where suitable p-dopants are metal oxides, for example $MoO_3$ or $WO_3$, or (per)fluorinated electron-deficient aromatic compounds. Further suitable p-dopants are HAT-CN (hexacyanohexaazatriphenylene) or the compound NPD9 from Novaled. A layer of this type simplifies hole injection in materials having a low HOMO energy, i.e. an HOMO energy with a large negative value.

In general, all materials which are used for the layers in accordance with the prior art can be used in the further layers of the electronic device.

The electronic device is correspondingly structured in a manner known per se, depending on the application, provided with contacts and finally hermetically sealed, since the lifetime of such devices is drastically shortened in the presence of water and/or air.

The formulations according to the invention and the electronic devices, in particular organic electroluminescent devices, obtainable therefrom are distinguished over the prior art by one or more of the following surprising advantages:

1. The electronic devices obtainable using the formulations according to the invention exhibit very high stability and a very long lifetime compared with electronic devices obtained using conventional methods.
2. The formulations according to the invention can be processed using conventional methods, so that cost advantages can also be achieved thereby.
3. The organic functional materials employed in the formulations according to the invention are not subject to any particular restrictions, enabling the process of the present invention to be employed comprehensively.
4. The layers obtainable using the formulations of the present invention exhibit excellent quality, in particular with respect to the uniformity of the layer.

These above-mentioned advantages are not accompanied by an impairment of the other electronic properties.

It should be pointed out that variations of the embodiments described in the present invention fall within the scope of this invention. Each feature disclosed in the present invention can, unless this is explicitly excluded, be replaced by alternative features which serve the same, an equivalent or a similar purpose. Thus, each feature disclosed in the present invention is, unless stated otherwise, to be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, are themselves inventive and are not to be regarded merely as part of the embodiments of the present invention. For these features, independent protection can be sought in addition or as an alternative to each invention presently claimed.

The teaching on technical action disclosed in the present invention can be abstracted and combined with other examples.

The invention is explained in greater detail below with reference to working examples, but without being restricted thereby.

The person skilled in the art will be able to use the descriptions to produce further formulations and electronic devices according to the invention without the need to employ inventive skill and thus can carry out the invention throughout the claimed range.

WORKING EXAMPLES

Five devices were made, using the device structure as shown in FIG. 1. A green emissive layer (G-EML) is prepared in a Reference and Examples 1, 2, 3 and 4. The solvents for G-EML are ethyl benzoate (Reference), cyclohexyl hexanoate (Example 1), cyclohexyl isovalerate (Example 2), menthyl isovalerate (Example 3), and menthyl acetate (Example 4). Table 2 summarizes the concentration, viscosity and surface tension of the inks containing G-EM1 as green emissive layer material.

TABLE 2

Concentration, viscosity and surface tension of the inks for G-EML.

| Layer | Ink Code | Conc. (g/L) | Viscosity (mPas) @25° C. | Surface tension (mN/m) @23.5° C. |
|---|---|---|---|---|
| G-EML | Reference | 14 | 2.3 | 34.4 |
| G-EML | Example 1 | 14 | 3.7 | 28.7 |
| G-EML | Example 2 | 14 | 3.3 | 27.6 |
| G-EML | Example 3 | 14 | 6.6 | 26.4 |
| G-EML | Example 4 | 14 | 4.2 | 27.0 |

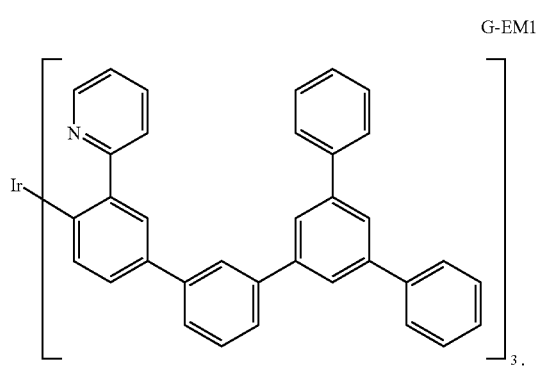

G-EM1

Table 3 shows the boiling point, surface tension and viscosity of the solvents used in the examples.

TABLE 3

Solvents used in the examples.

| Solvents | Boiling point (° C.) | Viscosity (mPas) @ 25° C. | Surface tension (mN/m) @ 23.5° C. |
|---|---|---|---|
| Ethyl benzoate, CAS: 93-89-0 | 212 | 2.1 | 34.5 |
| Cyclohexyl hexanoate, CAS 6243-10-3 | 255 | 3.4 | 28.7 |
| Cyclohexyl isovalerate, CAS 7774-44-9 | 223 | 3.0 | 27.5 |
| Menthyl isovalerate, CAS 16409-46-4 | 260 | 5.9 | 26.5 |
| Menthyl acetate, CAS 89-48-5 | 229 | 3.8 | 26.9 |

The viscosity of the formulations and solvents was measured using a 1° cone-plate rotational rheometer (type: Haake MARS III Rheometer from Thermo Scientific), where the temperature and sheer rate are exactly controlled. The viscosities given in Table 2 are the viscosities of each formulation measured at a temperature of 25° C. (+/−0.2° C.) and a sheer rate of 500 s$^{-1}$. The measurements were carried out with the following setup: Haake MARS III Rheometer with bottom plate TMP60 and cone C60/1° Ti L.; $N_2$ supply with a back-pressure of ~1.8 bar; sample volume of 1.3 mL. Each formulation is measured three times. The stated viscosity value is averaged over said measurements. The data processing is performed with the software "Haake RheoWin Job Manager" in accordance with DIN 1342-2. The equipment (Haake MARS III from Thermo Scientific) is regularly calibrated by Thermo Scientific and received a certified standard factory calibration before its first use.

The surface tension measurements were performed using the high precision drop shape analysis tool DSA100 from Krüss GmbH. The surface tension is determined by the software "DSA4" in accordance with DIN 55660-1. All measurements were performed at room temperature being in the range between 22° C. and 24° C. The standard operating procedure includes the determination of the surface tension of each formulation (sample volume of 0.3 mL) using a fresh disposable drop dispensing system (syringe and needle). Each drop is measured over the duration of one minute with sixty measurements which are later on averaged. For each formulation three drops are measured. The final value is averaged over said measurements. The tool is regularly cross-checked against various liquids having known surface tension.

Description of Fabrication Process

Glass substrates covered with pre-structured ITO and bank material were cleaned using ultrasonication in deionized water, then dried using an air-gun and a subsequent annealing on a hot-plate at 180° C. for 5 minutes. A hole-injection layer (HIL) was inkjet-printed onto the substrate and dried in vacuum. The HIL was then annealed at 180° C. for 30 minutes. On top of the HIL, a hole-transport layer (HTL) was inkjet-printed, dried in vacuum and annealed at 210° C. for 30 minutes. The green emissive layer (G-EML) was also inkjet-printed, vacuum dried and annealed at 160° C. for 10 minutes. All the inkjet printing processes were done under yellow light, in air and under ambient conditions. HIL annealing process was done in air; HTL and G-EML were annealed in nitrogen atmosphere. The devices were then transferred into the vacuum deposition chamber were the deposition of a blue common layer (BCL), an electron-transport layer (ETL), and a cathode (Al) was done using thermal evaporation. The devices were then encapsulated in a glove box and physical characterization was performed in ambient air. FIG. 1 shows the device structure. The device is driven with constant voltage provided by a Keithley 230 voltage source. The voltage over the LEP device as well as the current through the LEP device are measured with two Keithley 199 DMM multimeters. The brightness of the device is detected with a SPL-025Y brightness sensor, a combination of a photodiode with a photonic filter. The photo current is measured with a Keithley 617 electrometer. For the spectra, the brightness sensor is replaced by a glass fiber which is connected to the spectrometer input. The device lifetime is measured under a given current with an initial luminance. The luminance is then measured over time by a calibrated photodiode.

Results and Discussion

The efficiencies of the examples in this invention show comparable or higher values than the Reference. This indicates that the solvents in our examples show better film formation during drying. Our examples show comparable and better lifetime than the Reference, which clearly shows that there is no damage or bad effect of the new solvent system on the device performance. Table 4 summarizes the device efficiency and lifetime values. These solvent system provides better device performance and a wider process window which is essential to meet the different requirements of various ink-jet printing machines using different heads.

TABLE 4

Luminance efficiency, external quantum efficiency and power efficiency of the Reference and Examples 1 to 4.

|  | Luminance efficiency at 1000 cd/m² | External quantum efficiency at 1000 cd/m² | Power efficiency at 1000 cd/m² |
| --- | --- | --- | --- |
| Reference | 53.9 | 14.8 | 25.1 |
| Example 1 | 57.7 | 15.6 | 28.2 |
| Example 2 | 55.8 | 15.6 | 25.5 |
| Example 3 | 55.8 | 15.3 | 30.0 |
| Example 4 | 55.0 | 15.4 | 24.4 |

Additional Working Examples 5 to 11 and Reference 1

Eight devices were made using the device structure as shown in FIG. 2. Solvents such as menthyl isovalerate (menthoval) (CAS-Nr. 16409-46-4) and cyclohexyl hexanoate (CHH) (CAS-Nr. 6243-10-3) were used in G-EML inks and HTL inks. 3-Phenoxytoluene (3-PT) (CAS-Nr.: 3586-14-9) was used as a reference.

Table 5 summarizes the concentration, viscosity and surface tension of the inks used in these examples for preparing a hole-transport layer (HTL) or green emissive layer (G-EML).

TABLE 5

Concentration, viscosity and surface tension of the inks for HTL and G-EML.

| Layer | Solvent (CAS) | Conc. (weight %) | Viscosity (mPas) | Surface Tension (mN/m) | Remark |
| --- | --- | --- | --- | --- | --- |
| HTL | 3586-14-9 | 0.666 | 6.73 [a] | 37.8 [b] | Reference 1 Example 5 Example 6 |
| HTL | 16409-46-4 | 0.769 | 9.76 [a] | 26.9 [b] | Example 7 Example 9 |
| HTL | 6243-10-3 | 0.700 | 5.55 [a] | 28.0 [b] | Example 8 Example 10 Example 11 |
| G-EML | 3586-14-9 | 1.903 | 4.40 [a] | 37.8 [b] | Reference 1 Example 7 Example 8 |
| G-EML | 16409-46-4 | 2.198 | 5.92 [a] | 26.7 [b] | Example 5 Example 9 Example 11 |
| G-EML | 6243-10-3 | 2.000 | 3.46 [a] | 28.8 [b] | Example 6 Example 10 |

[a] measured at 23° C.;
[b] measured at 25° C.

Table 6 shows further details of the inks in Working Examples 5 to 11 and Reference 1.

TABLE 6

Further details of the inks used in the layers and devices of Working Examples 5 to 11 and Reference 1.

| Device | HTL ink solvent | G-EML ink solvent |
| --- | --- | --- |
| Reference 1 | 3586-14-9 | 3586-14-9 |
| Example 5 | 3586-14-9 | 16409-46-4 |
| Example 6 | 3586-14-9 | 6243-10-3 |
| Example 7 | 16409-46-4 | 3586-14-9 |
| Example 8 | 6243-10-3 | 3586-14-9 |
| Example 9 | 16409-46-4 | 16409-46-4 |
| Example 10 | 6243-10-3 | 6243-10-3 |
| Example 11 | 6243-10-3 | 16409-46-4 |

The viscosity of the formulations and solvents was measured using a 1 cone-plate rotational rheometer (type: Haake MARS III Rheometer from Thermo Scientific), where the temperature and sheer rate are exactly controlled. The viscosities given in Table 5 are the viscosities of each formulation measured at a temperature of 23.4° C. (+/−0.2° C.) and a sheer rate of 500 s$^{-1}$. The measurements were carried out with the following setup: Haake MARS III Rheometer with bottom plate TMP60 and cone C60/1° Ti L.; N$_2$ supply with a back-pressure of ~1.8 bar; sample volume of 1.3 mL. Each formulation is measured three times. The stated viscosity value is averaged over said measurements. The data processing is performed with the software "Haake RheoWin Job Manager" in accordance with DIN 1342-2. The equipment (Haake MARS III from Thermo Scientific) is regularly calibrated by Thermo Scientific and received a certified standard factory calibration before its first use.

The surface tension measurements were performed using the high precision drop shape analysis tool DSA100 from Krüss GmbH. The surface tension is determined by the software "DSA4" in accordance with DIN 55660-1. All measurements were performed at room temperature being in the range between 22° C. and 24° C. The standard operating procedure includes the determination of the surface tension of each formulation (sample volume of 0.3 mL) using a fresh disposable drop dispensing system (syringe and needle). Each drop is measured over the duration of one minute with sixty measurements which are later on averaged. For each formulation three drops are measured. The final value is averaged over said measurements. The tool is regularly cross-checked against various liquids having known surface tensions.

Description of the Fabrication Process

Glass substrates covered with pre-structured ITO and bank material were cleaned using ultrasonication in isopropanol followed by de-ionized water, then dried using an air-gun and a subsequent annealing on a hot-plate at 230° C. for 2 hours.

A hole-injection layer (HIL) using PEDOT-PSS (Clevios A14083, Heraeus) was inkjet-printed onto the substrate and dried in vacuum. The HIL was then annealed at 185° C. for 30 minutes in air.

On top of the HIL, a hole-transport layer (HTL) was inkjet-printed, dried in vacuum and annealed at 210° C. for 30 minutes in nitrogen atmosphere. As material for the hole-transport layer polymer HTM-1 was used. The structure of the polymer HTM-1 is the following:

The green emissive layer (G-EML) was also inkjet-printed, vacuum dried and annealed at 160° C. for 10 minutes in nitrogen atmosphere. The ink for the green emissive layer contained in all working examples two host materials (i.e. HM-1 and HM-2) as well as one triplett emitter (EM-1). The materials were used in the following ratio: HM-1:HM-2:EM-1=40:40:20. Only the solvent(s) differ from example to example, as can be seen from Tables 5 and 6 above. The structures of the materials are the following:

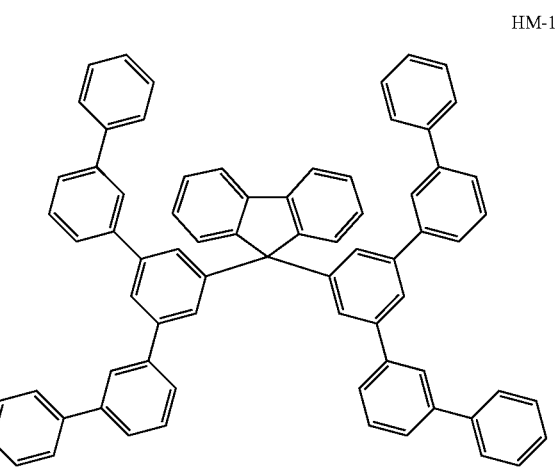

HM-1

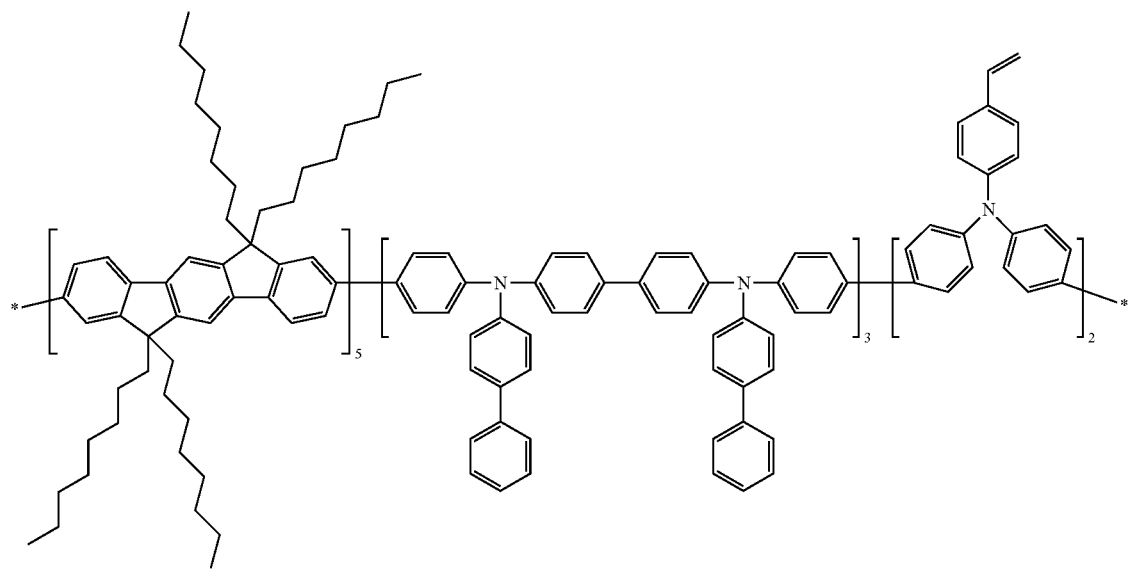

-continued

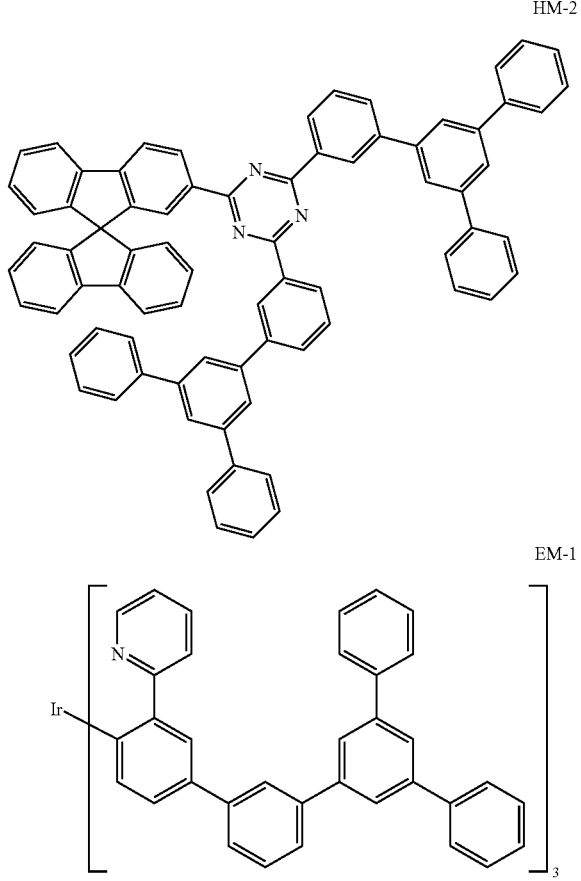

HM-2

EM-1

All the inkjet printing processes were performed under yellow light and under ambient conditions.

The devices were then transferred into the vacuum deposition chamber where the deposition of a common hole blocking layer (HBL), an electron-transport layer (ETL), and a cathode (Al) was performed using thermal evaporation (see FIG. 2). The devices were then characterized in the glovebox.

In the hole blocking layer (HBL) ETM-1 was used as a hole-blocking material. The material has the following structure:

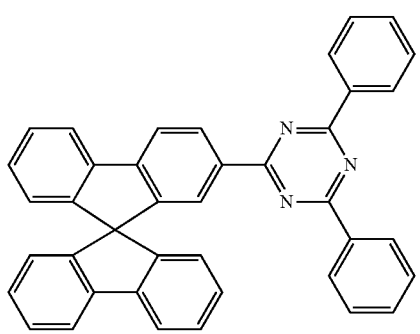

ETM-1

In the electron transport layer (ETL) a 50:50 mixture of ETM-1 and LiQ was used. LiQ is lithium 8-hydroxyquinolinate.

Finally, the Al electrode is vapor-deposited. The devices were then encapsulated in a glovebox and physical characterization was performed in ambient air.

FIG. 2 shows the device structure.

Measurement methods for Examples 5 to 11 and Reference 1 The devices are driven with constant voltage provided by a Keithley 230 voltage source. The voltage over the device as well as the current through the device are measured with two Keithley 199 DMM multimeters. The brightness of the device is detected with a SPL-025Y brightness sensor, a combination of a photodiode with a photonic filter. The photo current is measured with a Keithley 617 electrometer. For the spectra, the brightness sensor is replaced by a glass fiber which is connected to the spectrometer input. The device lifetime is measured under a given current with an initial luminance. The luminance is then measured over time by a calibrated photodiode.

Results and Discussion

Table 7 summarizes the luminance efficiency, voltage and lifetime. The device efficiencies show higher values with G-EML in Menthoval and CHH. These solvent systems provide a better film formation and morphology. It can also be seen in the decrease of operation voltages with Menthoval as the solvent, thanks to better electron/hole injection and transport in the devices. The device lifetime also improves dramatically with the better film and interface compared to the reference. When HTL is processed with Menthoval or CHH, the devices also show an improved performance. It demonstrates that the solvent systems also have a positive influence on HTL. These solvent systems provide a solution to achieve high efficiency and lifetime for ink-jet printing technology, in order to meet the application requirements and accelerate the development. It also provides an opportunity to fit various ink-jet printing machines using different heads.

TABLE 7

Luminance efficiency, operation voltage and device lifetime values.

| Device | Luminance efficiency at 1000 cd/m$^2$ (cd/A) | Operation voltage at 1000 cd/m$^2$ (V) | Lifetime (LT50) at 1000 cd/m$^2$ (khrs) |
|---|---|---|---|
| Reference 1 | 67.8 | 5.8 | 90 |
| Example 5 | 74.8 | 5.5 | 100 |
| Example 6 | 71.4 | 5.9 | 102 |
| Example 7 | 66.5 | 5.5 | 96 |
| Example 8 | 67.9 | 5.6 | 95 |
| Example 9 | 72.3 | 5.3 | 92 |
| Example 10 | 73 | 5.8 | 108 |
| Example 11 | 76.1 | 5.3 | 140 |

The invention claimed is:

1. A formulation comprising
at least one ester solvent according to General Formula (II):

General Formula (II)

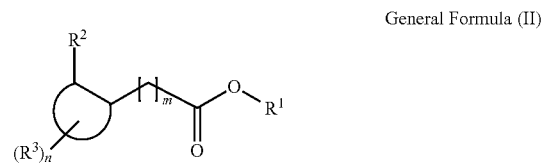

wherein

is a non-aromatic cyclic alkyl or alkenyl group having from 3 to 20 carbon atoms, to which the substituents $R^2$, $R^3$ and $-[CH_2]_m-O-CO-R^1$ or $-[CH_2]_m-CO-O-R^1$ are bound as shown in General Formulae (I) and (II), respectively, in which one or more hydrogen atoms may be optionally replaced by F and in which one or more non-adjacent $CH_2$ groups may be optionally replaced by $-O-$;
  $R^1$ and $R^2$ are the same or different from each other and are independently selected from the group consisting of hydrogen, straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atom may be optionally replaced by F and wherein one or more non-adjacent $CH_2$ groups may be optionally replaced by $-O-$ or $-Si(R^4)_2-$;
  $R^3$ is identical or different at each occurrence and is selected from the group consisting of straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by $-O-$ or $-Si(R^4)_2-$ and/or a plurality of $R^3$ may together form a mono- or polycyclic aliphatic ring system;
  $R^4$ is identical or different at each occurrence and is selected from the group consisting of hydrogen, straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by $-O-$, $-(C=O)-O-$ or $-(C=O)-$;
  m is an integer from 0 to 5; and
  n is an integer from 0 to 2x-2, wherein x is the number of carbon atoms in the non-aromatic cyclic alkyl or alkenyl group

;

and at least one organic functional material selected from the group consisting of organic conductors, organic semiconductors, organic fluorescent compounds, organic phosphorescent compounds, organic light-absorbent compounds, organic light-sensitive compounds, organic photosensitisation agents and other organic photoactive compounds, selected from organometallic complexes of transition metals, rare earths, lanthanides and actinides.

2. The formulation according to claim 1,
wherein

is a non-aromatic cyclic alkyl or alkenyl group having from 4 to 12 carbon atoms, to which the substituents $R^2$, $R^3$ and $-[CH_2]_m-O-CO-R^1$ or $-[CH_2]_m-CO-O-R^1$ are bound as shown in General Formulae (I) and (II), respectively, in which one or more hydrogen atoms may be optionally replaced by F and in which one or more non-adjacent $CH_2$ groups may be optionally replaced by $-O-$.

3. The formulation according to claim 1,
wherein

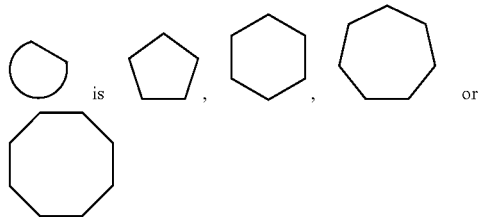

to which the substituents $R^2$, $R^3$ and $-[CH_2]_m-O-CO-R^1$ or $-[CH_2]_m-CO-O-R^1$ are bound as shown in General Formula (II).

4. The formulation according to claim 1, wherein $R^1$, $R^2$ and each of $R^3$ are independently selected from the group consisting of hydrogen and alkyl having from 1 to 10 carbon atoms with the provision that $R^3$ is not hydrogen.

5. The formulation according to claim 4, wherein $R^1$, $R^2$ and each of $R^3$ are independently selected from the group consisting of hydrogen, methyl, ethyl, 1-propyl, 2-propyl, n-butyl, iso-butyl, sec-butyl, t-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 3-methylpentyl, 4-methylpentyl, 2-methylpent-2-yl, 3-methylpent-2-yl, 2-methylpent-3-yl, 3-methylpent-3-yl, 2-ethylbutyl, 3-ethylbutyl, 2,3-dimethylbutyl, 2,3-dimethylbut-2-yl, 2,2-dimethylbutyl, n-heptyl, n-octyl, n-nonyl and n-decyl with the provision that $R^3$ is not hydrogen.

6. The formulation according to claim 1, wherein $R^4$ is identical or different at each occurrence and is selected from the group consisting of hydrogen, straight-chain alkyl or alkenyl groups having from 1 to 10 carbon atoms, branched-chain alkyl or alkenyl groups having from 3 to 10 carbon atoms, cyclic alkyl or alkenyl groups having from 3 to 10 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by $-O-$, $-(C=O)-O-$ or $-(C=O)-$.

7. The formulation according to claim 1, wherein the ester solvent is selected from the group consisting of:

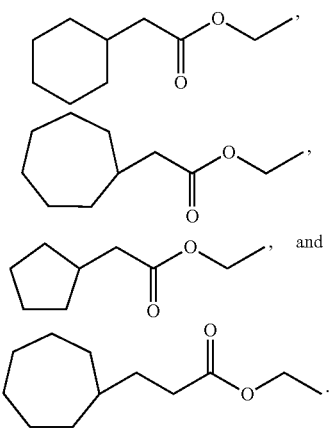

8. The formulation according to claim 1, wherein the ester solvent is liquid at room temperature.

9. The formulation according to claim 1, wherein the ester solvent has a boiling point of 400° C. or below, wherein the boiling point is given at 760 mm Hg.

10. The formulation according to claim 1, wherein the formulation has a surface tension in the range from 1 to 70 mN/m.

11. The formulation according to claim 1, wherein the formulation has a viscosity in the range from 0.8 to 50 mPas.

12. The formulation according to claim 1, wherein the content of the ester solvent is in the range from 0.01 to 99.99 vol.-% based on the total amount of solvents in the formulation.

13. The formulation according to claim 1, wherein the formulation contains at least one further solvent selected from the group consisting of substituted and non-substituted aromatic or linear esters; substituted and non-substituted aromatic or linear ethers; substituted or non-substituted arene derivatives; indane derivatives; substituted and non-substituted aromatic or linear ketones; substituted and non-substituted heterocycles, pyridines; fluorinated or chlorinated hydrocarbons; and linear or cyclic siloxanes.

14. The formulation according to claim 1, wherein the content of the organic functional material in the formulation is in the range from 0.001 to 20 weight-% based on the total weight of the formulation.

15. The formulation according to claim 1, wherein at least one organic functional material is selected from the group consisting of fluorescent emitters, phosphorescent emitters, host materials, matrix materials, exciton-blocking materials, electron-transport materials, electron-injection materials, hole-conductor materials, hole-injection materials, n-dopants, p-dopants, wide-band-gap materials, electron-blocking materials or hole-blocking materials.

16. The formulation according to claim 15, wherein the at least one organic functional material is selected from the group consisting of fluorescent emitters and phosphorescent emitters.

17. The formulation according to claim 16, wherein the organic functional material has a low molecular weight.

18. A process for the preparation of the formulation according to claim 1, wherein the ester solvent, the optional further solvent and the organic functional material are mixed.

19. A process for the production of an electronic device, which comprises applying the formulation according to claim 1 on a surface of at least one layer of the electronic device and subsequently dried.

20. A formulation comprising
at least one ester solvent according to General Formula (I):

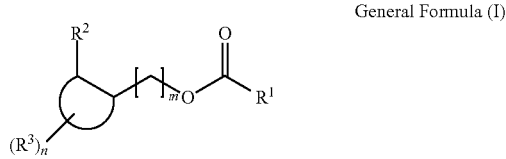

General Formula (I)

wherein

is a non-aromatic cyclic alkyl or alkenyl group having from 3 to 20 carbon atoms, to which the substituents $R^2$, $R^3$ and —$[CH_2]_m$—O—CO—$R^1$ or —$[CH_2]_m$—CO—O—$R^1$ are bound as shown in General Formulae (I) and (II), respectively, in which one or more hydrogen atoms may be optionally replaced by F and in which one or more non-adjacent $CH_2$ groups may be optionally replaced by —O—;

$R^1$ and $R^2$ are the same or different from each other and are independently selected from the group consisting of hydrogen, straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atom may be optionally replaced by F and wherein one or more non-adjacent $CH_2$ groups may be optionally replaced by —O— or —$Si(R^4)_2$—;

$R^3$ is identical or different at each occurrence and is selected from the group consisting of straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by —O— or —$Si(R^4)_2$— and/or a plurality of $R^3$ may together form a mono- or polycyclic aliphatic ring system;

$R^4$ is identical or different at each occurrence and is selected from the group consisting of hydrogen, straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by —O—, —(C=O)—O— or —(C=O)—;

m is an integer from 0 to 5; and n is an integer from 0 to 2x-2, wherein x is the number of carbon atoms in the non-aromatic cyclic alkyl or alkenyl group

and at least one organic functional material selected from the group consisting of organic conductors, organic semiconductors, organic fluorescent compounds, organic phosphorescent compounds, organic light-absorbent compounds, organic light-sensitive compounds, organic photosensitisation agents and other organic photoactive compounds, selected from organometallic complexes of transition metals, rare earths, lanthanides and actinides and wherein the content of the ester solvent is in the range from 0.01 to 99.99 vol.-% based on the total amount of solvents in the formulation.

21. A formulation comprising
at least one ester solvent according to General Formula (I):

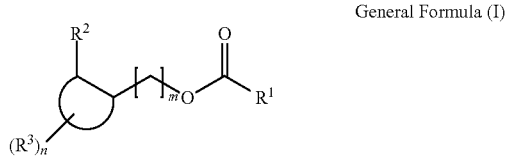

General Formula (I)

wherein

is a non-aromatic cyclic alkyl or alkenyl group having from 3 to 20 carbon atoms, to which the substituents $R^2$, $R^3$ and —[$CH_2$]$_m$—O—CO—$R^1$ or —[$CH_2$]$_m$—CO—O—$R^1$ are bound as shown in General Formulae (I) and (II), respectively, in which one or more hydrogen atoms may be optionally replaced by F and in which one or more non-adjacent $CH_2$ groups may be optionally replaced by —O—;

$R^1$ and $R^2$ are the same or different from each other and are independently selected from the group consisting of hydrogen, straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atom may be optionally replaced by F and wherein one or more non-adjacent $CH_2$ groups may be optionally replaced by —O— or —Si($R^4$)$_2$—;

$R^3$ is identical or different at each occurrence and is selected from the group consisting of straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by —O— or —Si($R^4$)$_2$— and/or a plurality of $R^3$ may together form a mono- or polycyclic aliphatic ring system;

$R^4$ is identical or different at each occurrence and is selected from the group consisting of hydrogen, straight-chain alkyl or alkenyl groups having from 1 to 20 carbon atoms, branched-chain alkyl or alkenyl groups having from 3 to 20 carbon atoms, cyclic alkyl or alkenyl groups having from 3 to 20 carbon atoms, and aryl or heteroaryl groups having from 4 to 6 carbon atoms, wherein one or more hydrogen atoms may be optionally replaced by F and wherein one or more non-adjacent $CH_2$ groups may be optionally replaced by —O—, —(C=O)—O— or —(C=O)—;

m is an integer from 0 to 5; and
n is an integer from 0 to 2x-2, wherein x is the number of carbon atoms in the non-aromatic cyclic alkyl or alkenyl group

and at least one organic functional material selected from the group consisting of organic conductors, organic semiconductors, organic fluorescent compounds, organic phosphorescent compounds, organic light-absorbent compounds, organic light-sensitive compounds, organic photosensitisation agents and other organic photoactive compounds, selected from organometallic complexes of transition metals, rare earths, lanthanides and actinides and wherein the formulation contains at least one further solvent selected from the group consisting of substituted and non-substituted aromatic or linear esters; substituted and non-substituted aromatic or linear ethers; substituted or non-substituted arene derivatives; indane derivatives; substituted and non-substituted aromatic or linear ketones; substituted and non-substituted heterocycles, pyridines; fluorinated or chlorinated hydrocarbons; and linear or cyclic siloxanes.

* * * * *